United States Patent
Miron et al.

(10) Patent No.: US 8,906,620 B2
(45) Date of Patent: Dec. 9, 2014

(54) EXON GROUPING ANALYSIS

(75) Inventors: Alexander Miron, Chestnut Hill, MA (US); J. Dirk Iglehart, Newton, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 949 days.

(21) Appl. No.: 12/077,966

(22) Filed: Mar. 24, 2008

(65) Prior Publication Data

US 2009/0191547 A1 Jul. 30, 2009

Related U.S. Application Data

(60) Provisional application No. 60/919,810, filed on Mar. 23, 2007.

(51) Int. Cl.
*C12Q 1/68* (2006.01)
*C12P 19/34* (2006.01)

(52) U.S. Cl.
CPC .................................. *C12Q 1/6827* (2013.01)
USPC ........................... 435/6.12; 435/6.1; 435/6.11

(58) Field of Classification Search
None
See application file for complete search history.

(56) References Cited

U.S. PATENT DOCUMENTS

2003/0022190 A1 1/2003 Shipman et al. .................. 435/6

FOREIGN PATENT DOCUMENTS

| EP | 1 736 554 A2 | 12/2006 |
|---|---|---|
| WO | WO 2006/119439 A2 | 11/2006 |

OTHER PUBLICATIONS

Esteban-Cardenosa et al., "High-Throughput Mutation Detection Method to Scan BRCA1 and BRCA2 Based on Heteroduplex Analysis by Capillary Array Electorphoresis," Clinical Chemistry, 2004, vol. 50, No. 2, pp. 313-320.*
Marian, Hill, "Conformation-Sensitive Gel Electrophoresis," Medical Biomethods Handbook, Humana Press, 2005, pp. 147-153.*
Goth et al., "A Simple PCR-Heteroduplex Screening Method for Detection of Common Mutation of the Catalase Gene in Hungary," Clinical Chemistry, 2000, vol. 46, No. 8, pp. 1199-1200.*
Ganguly, A., "An Update on Conformation Sensitive Gel Electrophoresis", *Hum. Mutation*, 1 (4):334-342 (2002).
Golshan et al., "The prevalence of germline BRCA1 and BRCA2 mutations in young women with breast cancer undergoing breast-conservation therapy", *Am. J. Surg.*, 192(1):58-62 (2006).
Infante et al., "High proportion of novel mutations of BRCA1 and BRCA2 in breast/ovarian cancer patients from Castilla-León (central Spain)", *J. Hum. Genet.*, 51(7):611-617 (2006).
Körkkö et al., "Conformation sensitive gel electrophoresis for simple and accurate detection of mutations: Comparison with denaturing gradient gel electrophoresis and nucleotide sequencing", *Proc. Natl. Acad. Sci. U.S.A.*, 95(4):1681-1685 (1998).
Velasco et al., "Rapid mutation detection in complex genes by heteroduplex analysis with capillary array electrophoresis", *Electrophoresis*, 26(13):2539-2552 (2005).
Botstein et al., "Construction of a Genetic Linkage Map in Man Using Restriction Fragment Length Polymorphisms", *Am. J. Hum. Genet.*, 32:314-331 (1980).
Brownie et al., "The elimination of primer-dimer accumulation in PCR", *Nucl. Acids Res.*, 25(16):3235-3241 (1997).

(Continued)

*Primary Examiner* — Young J Kim
(74) *Attorney, Agent, or Firm* — Cooley LLP

(57) ABSTRACT

This invention pertains to the identification of specific disease-causing DNA sequences in a subject. The methods of the present invention can be used to identify genetic alterations, to determine the molecular basis for genetic diseases, and to provide carrier and prenatal diagnosis for genetic counseling.

30 Claims, 17 Drawing Sheets

(56) References Cited

OTHER PUBLICATIONS

Highsmith, Jr. et al., "Use of a DNA toolbox for the characterization of mutation scanning methods. I: Construction of the toolbox and evaluation of heteroduplex analysis", *Electrophoresis*, 20(6):1186-1194 (1999).

Korkko et al., "Conformation sensitive gel electrophoresis for simple and accurate detection of mutations: comparison with denaturing gradient gel electrophoresis and nucleotide sequencing", *Proc. Natl. Acad. Sci. U.S.A.*, 95(4):1681-1685 (1998).

Nakamura et al., "Variable Number of Tandem Repeat (VNTR) Markers for Human Gene Mapping", *Science*, 235:1616-1622 (1987).

Rozen and Skaletsky, "Primer3 on the WWW for general users and for biologist programmers", *Meth. Mol. Biol.*, 132:365-386 (2000).

\* cited by examiner

DNA TOOL BOX
Electrophoresis 1999 Jun;20(6):1186-94

Control : A remains A
Mutations : A to T, A to G, A to C

```
                      SEQUENCE LISTING

<160> NUMBER OF SEQ ID NOS: 16

<210> SEQ ID NO 1
<211> LENGTH: 26
<212> TYPE: DNA
<213> ORGANISM: Artificial sequence
<220> FEATURE:
<223> OTHER INFORMATION: Chemically synthesized primer

<400> SEQUENCE: 1
gcgtactagc gtaccacgtg tcgact                                          26

<210> SEQ ID NO 2
<211> LENGTH: 26
<212> TYPE: DNA
<213> ORGANISM: Artificial sequence
<220> FEATURE:
<223> OTHER INFORMATION: Chemically synthesized primer

<400> SEQUENCE: 2
gacgatacga cgggcgtact agcgta                                          26

<210> SEQ ID NO 3
<211> LENGTH: 42
<212> TYPE: DNA
<213> ORGANISM: Artificial sequence
<220> FEATURE:
<223> OTHER INFORMATION: Chemically synthesized primer

<400> SEQUENCE: 3
gtaatacgac tcactatagg ggcgtactag cgtaccacgt gt                        42

<210> SEQ ID NO 4
<211> LENGTH: 42
<212> TYPE: DNA
<213> ORGANISM: Artificial sequence
<220> FEATURE:
<223> OTHER INFORMATION: Chemically synthesized primer

<400> SEQUENCE: 4
gattaaccct cactaaaggg agacgatacg acgggcgtac ta                        42

<210> SEQ ID NO 5
<211> LENGTH: 20
<212> TYPE: DNA
<213> ORGANISM: Artificial sequence
```

```
<220> FEATURE:
<223> OTHER INFORMATION: Chemically synthesized primer

<400> SEQUENCE: 5
taatacgact cactataggg                                                      20

<210> SEQ ID NO 6
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 6
attaaccctc actaaaggga                                                      20

<210> SEQ ID NO 7
<211> LENGTH: 26
<212> TYPE: DNA
<213> ORGANISM: Artificial sequence
<220> FEATURE:
<223> OTHER INFORMATION: Chemically synthesized primer

<400> SEQUENCE: 7
gcgtactagc gtaccacgtg tcgact                                               26

<210> SEQ ID NO 8
<211> LENGTH: 26
<212> TYPE: DNA
<213> ORGANISM: Artificial sequence
<220> FEATURE:
<223> OTHER INFORMATION: Chemically synthesized primer

<400> SEQUENCE: 8
gacgatacga cgggcgtact agcgta                                               26

<210> SEQ ID NO 9
<211> LENGTH: 42
<212> TYPE: DNA
<213> ORGANISM: Artificial sequence
<220> FEATURE:
<223> OTHER INFORMATION: Chemically synthesized primer

<400> SEQUENCE: 9
gtaatacgac tcactatagg ggcgtactag cgtaccacgt gt                             42

<210> SEQ ID NO 10
<211> LENGTH: 42
<212> TYPE: DNA
<213> ORGANISM: Artificial sequence
<220> FEATURE:
<223> OTHER INFORMATION: Chemically synthesized primer

<400> SEQUENCE: 10
gattaaccct cactaaaggg agacgatacg acgggcgtac ta                             42

<210> SEQ ID NO 11
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 11
taatacgact cactataggg                                                      20
```

```
<210> SEQ ID NO 12
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 12
attaaccctc actaaaggga                                                  20

<210> SEQ ID NO 13
<211> LENGTH: 11
<212> TYPE: DNA
<213> ORGANISM: Artificial sequence
<220> FEATURE:
<223> OTHER INFORMATION: Chemically synthesized peptide
<220> FEATURE:
<221> NAME/KEY: misc_feature
<222> LOCATION: (1)..(5)
<223> OTHER INFORMATION: n is a, c, g, t or u
<220> FEATURE:
<221> NAME/KEY: misc_feature
<222> LOCATION: (7)..(11)
<223> OTHER INFORMATION: n is a, c, g, t or u

<400> SEQUENCE: 13
nnnnnannnn n                                                           11

<210> SEQ ID NO 14
<211> LENGTH: 11
<212> TYPE: DNA
<213> ORGANISM: Artificial sequence
<220> FEATURE:
<223> OTHER INFORMATION: Chemically synthesized peptide
<220> FEATURE:
<221> NAME/KEY: misc_feature
<222> LOCATION: (1)..(5)
<223> OTHER INFORMATION: n is a, c, g, t or u
<220> FEATURE:
<221> NAME/KEY: misc_feature
<222> LOCATION: (7)..(11)
<223> OTHER INFORMATION: n is a, c, g, t or u

<400> SEQUENCE: 14
nnnnngnnnn n                                                           11

<210> SEQ ID NO 15
<211> LENGTH: 11
<212> TYPE: DNA
<213> ORGANISM: Artificial sequence
<220> FEATURE:
<223> OTHER INFORMATION: Chemically synthesized peptide
<220> FEATURE:
<221> NAME/KEY: misc_feature
<222> LOCATION: (1)..(5)
<223> OTHER INFORMATION: n is a, c, g, t or u
<220> FEATURE:
<221> NAME/KEY: misc_feature
<222> LOCATION: (7)..(11)
<223> OTHER INFORMATION: n is a, c, g, t or u

<400> SEQUENCE: 15
nnnnncnnnn n                                                           11

<210> SEQ ID NO 16
<211> LENGTH: 11
<212> TYPE: DNA
<213> ORGANISM: Artificial sequence
<220> FEATURE:
<223> OTHER INFORMATION: Chemically synthesized peptide
```

```
<220> FEATURE:
<221> NAME/KEY: misc_feature
<222> LOCATION: (1)..(5)
<223> OTHER INFORMATION: n is a, c, g, t or u
<220> FEATURE:
<221> NAME/KEY: misc_feature
<222> LOCATION: (7)..(11)
<223> OTHER INFORMATION: n is a, c, g, t or u

<400> SEQUENCE: 16
nnnnntnnnn n                                                        11
```

EXON GROUPING ANALYSIS

RELATED APPLICATIONS

This application claims the benefit of U.S. Ser. No. 60/919,810, filed Mar. 23, 2007 the contents of which is incorporated herein by reference in its entirety.

INCORPORATION-BY-REFERENCE OF SEQUENCE LISTING

The contents of the text file named "DFCI_042_001US_SubSeqList.txt", which was created on Jul. 30, 2014 and is 8 KB in size, are hereby incorporated by reference in their entirety.

BACKGROUND OF THE INVENTION

Genomic DNA varies significantly from individual to individual, except in identical siblings. Many human diseases arise from genomic variations and mutations. The genetic diversity amongst humans and other life forms explains the heritable variations observed in disease susceptibility. Diseases arising from such genetic mutations include Huntington's disease, cystic fibrosis and Duchenne muscular dystrophy. Each of these diseases is associated with a single gene mutation. Diseases such as multiple sclerosis, diabetes, Parkinson's disease, Alzheimer's disease, hypertension and cancer (e.g., Breast Cancer) are much more complex. These diseases may be due to polygenic (multiple gene influences) or multifactorial (multiple gene and environmental influences) causes. Many of the variations in the genome do not result in a disease trait. However, as described above, a single mutation can result in a disease trait. The ability to scan the human genome to identify the location of genes which underlie or are associated with the pathology of such diseases is an enormously powerful tool in medicine and human biology.

Although substantial progress has been made in identifying the genetic basis of many human diseases, current methodologies used to develop this information are limited by prohibitive costs and the extensive amount of work required to obtain genotype information from large sample populations. These limitations make identification of complex gene mutations contributing to disorders such as diabetes extremely difficult. Techniques for scanning the human genome to identify the locations of genes involved in disease processes began in the early 1980s with the use of restriction fragment length polymorphism (RFLP) analysis (Botstein et al. (1980), Am. J. Hum. Genet., 32:314-31; Nakamura et al. (1987), Science, 235:1616-22). RFLP analysis involves southern blotting and other techniques. Southern blotting is both expensive and time-consuming when performed on large numbers of samples, such as those required to identify a complex genotype associated with a particular phenotype. Some of these problems were avoided with the development of polymerase chain reaction (PCR) based microsatellite marker analysis. Microsatellite markers are simple sequence length polymorphisms (SSLPs) consisting of di-, tri-, and tetra-nucleotide repeats.

Oncology is another field that relies heavily on the discovery of DNA alterations. The discovery of mutations in DNA leads to the identification of mutated proteins in the tumors. The specific lesions in the proteins from tumor samples are used to develop drugs which attack and destroy only the cancer cells that contain those DNA mutations. This results in personalized, non-toxic therapy that will one day cure cancer. It is imperative to identify these targets by genome scale analysis of every protein coding region.

Other methods for detecting mutations are also prohibitively expensive and impractical. One of these methods involves DNA sequencing. A complete analysis by DNA sequencing may involve sequencing 6 billion bases of nucleic acid per diagnosis. While such an analysis is possible with current technology, the cost associated with the analysis of 6 billion bases is at this time prohibitive for routine diagnosis outside of the research environment.

Another mutation analyzing method involves DNA chips. A number of oligonucleotides can be fixed onto a solid glass surface and selectively hybridized with a test DNA fragment to detecting a signal and determine a nucleic acid sequence. While this technique is possible for common (Single Nucleotide Polymorphisms or SNP's) and known mutations, it is not economically feasible for unknown DNA mutations that may occur in a gene. It is also not practical for the detection of insertions and deletions in DNA. For example, in cystic fibrosis, a recessive disorder affecting 1 in 2000-2500 live births in the United States, more than 225 presumed disease-causing mutations have been identified in one gene alone. Any one of these 225 mutations may cause a person to be a carrier or a sufferer of cystic fibrosis.

Another approach to mutation scanning relies on the fact that DNA molecules change in structure depending on the exact content of base-pairs. The structural defects in the DNA can be measured by looking for altered mobility of the DNA fragment through either a polyacrylamide gel, a capillary filled with flowable linear polyacrylamide or denaturing liquid chromatography. The analysis can be done on single strand molecules (Single Strand Conformational Analysis) or on double stranded molecules (Heteroduplex Analysis, Temperature Sensitive Gradient Electrophoresis, Conformation Specific Gel Elecrophoresis or Denaturing High Performance Liquid Chromatography).

Each of the methods described above, and variations thereof, are limited in their applicability to complex mutational analysis. Specifically, tumor samples are contaminated with normal cells (lymphocytes, stroma, etc.) which results in heterogeneous, impure DNA populations and makes it quite difficult to find mutations with the current gold standard of DNA sequencing. Moreover, the current techniques suffer from large costs and lack of sensitivity in non-pure DNA in the case of DNA sequencing and low sensitivity and throughput in the case of the structural analysis based methods. Additionally all these procedures suffer from low throughput which limits the utility and scope of analysis. Furthermore, multiple mutations may be present in a single affected individual, and may be spaced within a few base pairs of each other. These phenomena present unique difficulties in designing clinical screening methods that can accommodate large numbers of sample DNAs.

Thus, there is a need in the art for relatively low cost methods that allow the efficient screening of large numbers of target DNA such as disease associated genes and exons, for genetic variation and the rapid identification of the variant sequence. This extremely important in both risk analysis from blood samples as well as drug target identification and design from tumor samples.

SUMMARY OF THE INVENTION

The present invention (referred to herein as Exon Grouping Analysis or EGAN)) enables simple, high throughput, and rapid examination of mutations in many target regions of a nucleic acid simultaneously by amplifying the target regions by multiplex PCR and analyzing the amplified products produced by the PCR by conformation dependent electrophoresis. As many as 100 target regions in 95 people can be examined simultaneously on one EGAN gel. In an optional step, any mutations or polymorphisms detected may be further analyzed by DNA sequence. Thus, the present invention provides methods for examining two, four, eight, forty up to 300,000 (including every gene in the human genome) sites for possible mutations.

In order to analyze mutations, EGAN amplifies target regions of DNA that contain possible mutations for subsequent analysis. The target regions of DNA may include, for example, genes that are known to cause the symptoms of a disease in an individual. These sites may include, for example, the BRCA1 and BRCA2 gene in a breast cancer tumor sample, the β-globin gene of a sickle-cell anemia patient, the cystic fibrosis transmembrane conductance regulator gene in a cystic fibrosis patient, the human beta globin gene in β-thalassemia patients, and the glucocerebrosidase gene for patients with Gaucher's disease. It could also include the analysis of tumor DNA By analyzing the gene and detecting a mutation in the gene, a diagnosis of a disease may be made or confirmed.

This procedure can also be used to determine alterations in any tumor sample to guide drug development as well as therapy decisions. Moreover, EGAN is applicable to the analysis of DNA in humans as well as model organisms (mouse, drosophila, zebra fish, C. Elegans, viruses, bacteria etc.) in order to obtain genotype information to explain particular phenotypes in these organisms.

One embodiment of the invention is directed to a method for detecting one or more sequence changes in a plurality of target nucleic acid sequences in a nucleic acid sample (referred to herein as the EGAN method or EGAN analysis).

The EGAN method comprising the first step of (a) performing a multiplexed PCR reaction on the nucleic acid sample in the presence of a plurality of target specific PCR primer pairs. Each of the primer pairs comprises a first and second target specific primer. The first and second target specific primers are specific for one of the plurality of target nucleic acid sequences so that the multiplexed PCR reaction generates a plurality of amplified products. In addition, the first target specific primer of each primer pair comprises a first 5' region which contains the same sequence for all first primers and a first 3' region which is specific for (and which can be used for the amplification of) one of the plurality of target nucleic acid sequences. The second target specific primer comprises a first 5' region which contains the same sequence for all second primers and a second 3' region specific for (and which can be used for the amplification of) one of the plurality of target nucleic acid sequences.

The second step involves performing a PCR reaction on the plurality of amplified products with a first and second amplified product specific primer which is specific for said plurality of amplified products. In this PCR reaction, the first amplified product specific primer comprises a 3' region identical to the first 5' region of the first target specific primer, and the second amplified product specific primer comprises a 3' region identical to the second 5' region of the second target specific primer.

In the third step, homoduplexes and heteroduplexes are generated from the amplified products.

In the fourth step, the presence of the heteroduplexes is detected as an indicator of the one or more sequence changes.

The method may further comprise an optional step of determining the nucleic acid sequence of the homoduplexes and heteroduplexes to determine the one or more sequence changes. In this step, after the homoduplexes and heteroduplexes are identified, they are sequenced. Sequencing may involve, for example, sequencing the amplified product (homoduplexes or heteroduplexes or both) or the target nucleic acid. Sequencing is a well known technique and can involve, in some cases, elongation of target nucleic acids using a primer. The primer or primers used in sequencing includes, at least, any primer described in this specification including a target specific primer or an amplified product specific primer.

In this method, the first and second steps can be performed simultaneously in the same reaction, or the first and second steps may be performed in different reactions. It is noted that different reactions may be performed in the same tube sequentially.

In a preferred embodiment, each target specific PCR primer pair produces an amplified product in a PCR reaction of a different length than each other target specific PCR primer pair. In this manner, the products of one multiplexed PCR reaction may be analyzed in one electrophoresis lane of a gel because each product would have a different migration speed under electrophoresis.

The method may be performed with at least 5 target specific primer pairs, at least 10 target specific primer pairs, at least 20 target specific primer pairs, at least 30 target specific primer pairs, at least 40 target specific primer pairs, at least 60 target specific primer pairs, at least 80 target specific primer pairs, or at least 100 target specific primer pairs.

The plurality of amplified products produced by the methods of the invention may be of any size. In a preferred embodiment, the amplified products are between 200 to 800 bp in length.

If the 5' region of the first target specific primer is identical to the 5' region of the second target specific primer, step two (the amplification of the plurality of amplified products) may be performed with only one amplified product specific primer. That is, the first amplified product specific primer and the second amplified product specific primer may be identical in a 3' region. In fact, in this case, first amplified product specific primer and the second amplified product specific primer may be completely identical.

Any of the primers and nucleotides used in the PCR reaction of any step of the invention may comprise a detectable label. The detectable label may be a detachable label. For example, the detectable label may be heat labile, or light sensitive such that the label is detached or inactivated when exposed to heat, light or both. The detectable label may be selected from the group consisting of a fluorophore, an enzyme, a quencher, an enzyme inhibitor, a radioactive label, a member of a binding pair, and a combination thereof.

In one preferred embodiment, the step of generating homoduplexes and heteroduplexes from the amplified product may involve the substeps of (c1) denaturing the plurality of amplified products to form single stranded amplified products; and (c2) annealing said single stranded amplified products to each other to form homoduplexes and heteroduplexes. In a preferred embodiment, denaturing may be performed by heating the amplified products. Annealing may be performed by incubating the amplified products at 68° C. for 30 minutes. Other methods of denaturing and annealing, by adjusting the pH of a nucleic acid solution reaction are also known.

In one preferred embodiment, the step of detecting the presence of heteroduplexes may comprise the substep of detecting a difference in migration speed between the homoduplexes and the heteroduplexes under conformation sensitive gel electrophoresis. Conformation sensitive gel electrophoresis may be performed, for example, in a capillary containing a flowable polymer (e.g., capillary electrophoresis). Conformation sensitive gel electrophoresis may be performed in a gel comprising polyacrylamide with a 99 to 1 ratio of acrylamide to BAP, 15% formamide, and 1×TBE. Further, the polyacrylamide may be at a concentration of between 6% to 15%.

The one or more sequence changes, detected by any of the methods of the invention, may be selected from the group consisting of an alteration of one or more bases, an insertion of one or more bases, a deletion of one or more bases, and combinations thereof.

The method may use any DNA, RNA (including mRNA, hnRNA) as the target nucleic acid.

In one embodiment the starting material, the target nucleic acid, is isolated from a patient suspected of a genetic disease. The genetic disease may be selected from the group consisting of cancer, cystic fibrosis, sickle-cell anemia, beta-thalassemia, and Gaucher's disease. Alternatively, the target nucleic acid may be a part of a gene selected from the group consisting of an oncogene, beta-globin, cystic fibrosis transmembrane conductance regulator receptor, glucocerebrosidase and a combination thereof.

The method of the invention may be used to detect one or more sequence changes in at least one oncogene. The oncogene may be BRCA1, BRCA2, RAS, or and a combination thereof.

Another embodiment of the invention is directed to a method for detecting one or more sequence changes in a diseased tissue. The first step of the method involves performing EGAN analysis on a nucleic acid sample isolated from the diseased tissue to detect the presences of diseased tissue heteroduplexes and homoduplexes. The second step of the method involves performing EGAN analysis on a nucleic acid sample isolated from a normal tissue to detect the presence of normal tissue heteroduplexes and homoduplexes. The third step involves comparing the heteroduplexes and homoduplexes of the first step with the heteroduplexes and homoduplexes of the second step to determine a difference which is indicative of one or more sequence changes. The first two steps of this method may be performed in any order. In this method, the diseased tissue and the normal tissue may be from the same subject or from different subjects. A subject may be any animal or organism, including humans. Further, the diseased tissue and the normal tissue may be of the same tissue type or from different tissue types.

DETAILED DESCRIPTION OF THE INVENTION

Figure 1:
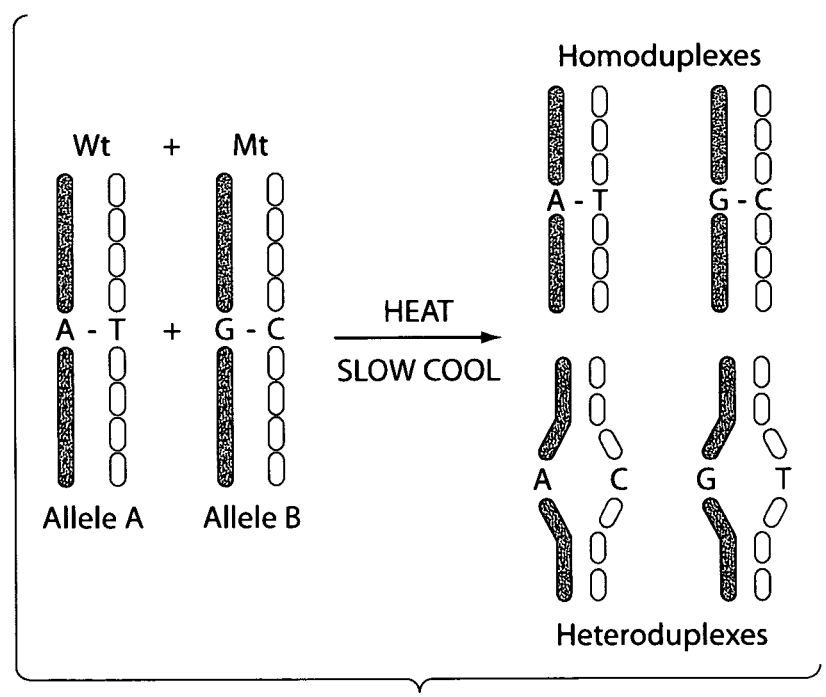
FIG. 1 depicts one of the many methods for the formation of DNA homoduplexes and heteroduplexes. In this method, homoduplexes and heteroduplexes are formed by heat and slow cooling.

The present invention (referred to herein as Exon Grouping Analysis or EGAN) encompasses a high-throughput method for detecting nucleic acid mutations and polymorphisms of specific nucleic acids sequences in nucleic acids isolated from a patient or any other organism of interest.

1. Starting Material

The starting material for EGAN may be DNA (e.g., genomic DNA, mitochondrial DNA) or RNA (e.g., mRNA, structural RNA, genomic RNA from a virus). Preferably, the nucleic acid to be analyzed comprises a portion of a particular gene or genetic locus in a patient's genomic DNA known to be involved in a pathological condition or syndrome. Non-limiting examples of pathological conditions and syndromes include cancer, cystic fibrosis, sickle-cell anemia, β-thalas-semia, and Gaucher's disease. It is understood that in some pathological conditions such as cancer, only the affected cells (e.g., cancer cells, tumor) would contain the cancerous mutation (e.g., activated oncogene) while cells and DNA isolated from other parts of the patient (e.g., germ cells, non tumor cells) would not have the mutations. In another aspect, the DNA to be analyzed may comprise part of a particular gene or genetic locus that may not be known to be linked to a particular disease, but in which polymorphism and linkage to a disease is known or suspected.

The nucleic acid used as starting material may be obtained from any cell source or body fluid. Methods for converting RNA into DNA, such as, for example, by the use of reverse transcriptase with oligo-dT or random primers are known. Non-limiting examples of cell sources available in clinical practice include blood cells, buccal cells, cervicovaginal cells, epithelial cells from urine, fetal cells, or any cells present in tissue obtained by biopsy including tumor cells. Body fluids include blood, urine, cerebrospinal fluid, and tissue exudates at the site of infection or inflammation. If desired, DNA is extracted from the cell source or body fluid using any of the numerous methods that are standard in the art. It will be understood that the particular method used to extract DNA will depend on the nature of the source. The minimum amount of DNA to be extracted for use in the present invention is about 5 picograms (corresponding roughly to about 1 cell equivalent of a genome size of 3 billion haploid DNA bases). It is noted that extraction is not absolutely necessary. The DNA to be analyzed may be amplified in situ by PCR or other amplification techniques using target specific primers or random primers.

Once extracted, the target nucleic acid may be employed in the present invention without further manipulation. Alternatively, one or more specific DNA regions present in the target DNA may be amplified by PCR. For example, the DNA of the BRCA1 gene may be amplified using PCR primers which span the complete gene. As it is known in the art, the amplified regions are specified by the choice of particular flanking sequences for use as primers. Amplification at this step provides the advantage of increasing the concentration of specific DNA sequences within the target DNA sequence population. This amplification is especially desirable if the amount of starting material is small.

2. Method for Detecting One or More Sequence Changes in Nucleic Acid

The method of the invention is directed to a method for detecting one or more sequence changes in a plurality of target nucleic acid sequences in a nucleic acid sample comprising four steps. Each of the steps is discussed in more detail below.

2a. Step (a)—PCR Amplification of Target Nucleic Acids

In step (a) PCR is performed on a nucleic acid sample to amplify regions of interest for subsequent EGAN analysis. Target nucleic acids are regions of the genome which is analyzed for mutations. The target nucleic acids will differ depending on the diagnosis desired. For example, for tumor tissue, one may wish to determine if there has been an oncogene mutation or activation. In this case, the target nucleic acids may be oncogenes and oncogene exons.

Figure 3:
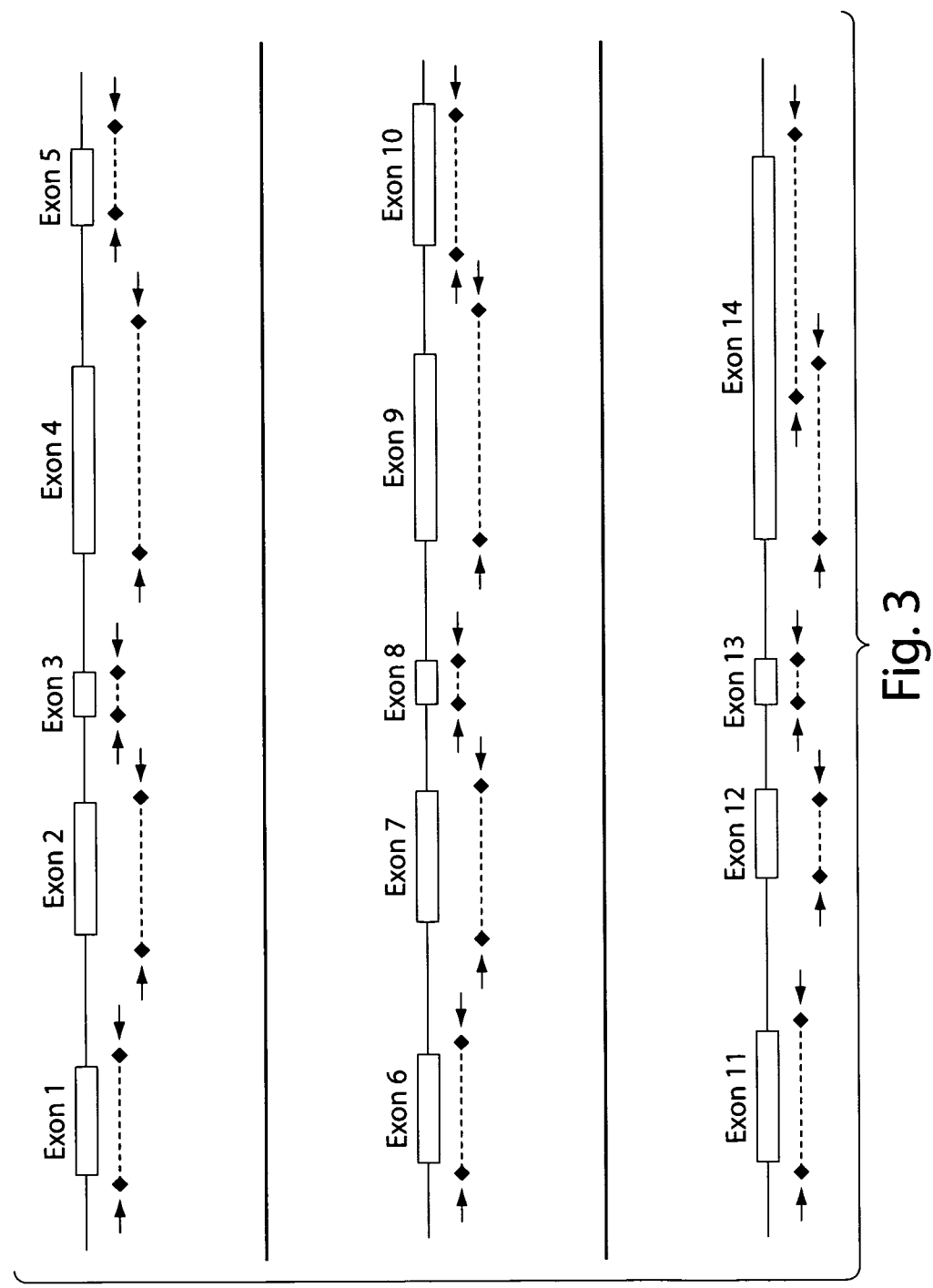
FIG. 3 is a schematic of primer design leading to high throughput exon grouping of a sample 14 exon gene. An example is shown of primer pair selection and fluorescent labeling using three dye sets (A. Ned; B. Fam; C. Vic). Each of the primer pairs is selected to amplify products of variable lengths to allow mixing and visualization in the same lane of an Exon Grouping Analysis (EGAN) gel. Since the three dye sets fluoresce at different wavelengths they can be mixed and visualized in that same lane of the gel. This packing can be extended to at least 25 exons per lane.

Target nucleic acids are amplified using PCR. Each target nucleic acid (e.g., each oncogene exon) may be targeted by a specific target specific primer pair. Each target specific primer pair comprises two primers—a first target specific primer and a second target specific primer. The target specific primer pairs are designed such that successful amplification using the target specific primer pair will generate an amplified product of a size that is different from an amplified product generated from any other target specific primer pair. For example, a first target specific primer pair may be specific for the first exon of the BRCA1 gene and generate an amplified product of 500 bps in size. A second target specific primer pair may be specific for the second exon of the BRCA1 gene and generate an amplified product of 550 bp in size. In this way, the amplified product generated from the first primer pair would have a sequence length (500 bp) which is different from the sequence length (550 bp) of the amplified product generated from the second primer pair. An example is shown in FIG. 3 of primers selected against 5 exons in each dye set (A. Ned; B. Fam; C. Vic). Each of the 5 primer pairs is selected to amplify products of variable lengths to allow mixing and visualization in the same lane of an Exon Grouping Analysis (EGAN) gel. Since the three dye sets fluoresce at different wavelengths they can also be mixed and visualized in that same lane of the gel. This packing can be extended to at least 24 exons per lane. This allows for mixing the products prior to gel analysis (See FIG. 4). It is noted that the above example with 5 primer pairs is for purposes of illustration, amplification may be performed with at least 20, at least 30, at least 40, at least 60, at least 80, or at least 100 primer pairs.

As discussed above the initial PCR reaction contains a plurality of target specific primers pairs where each primer pair contains a first primer and a second primer. The structure of each primer is now described.

Figure 2:
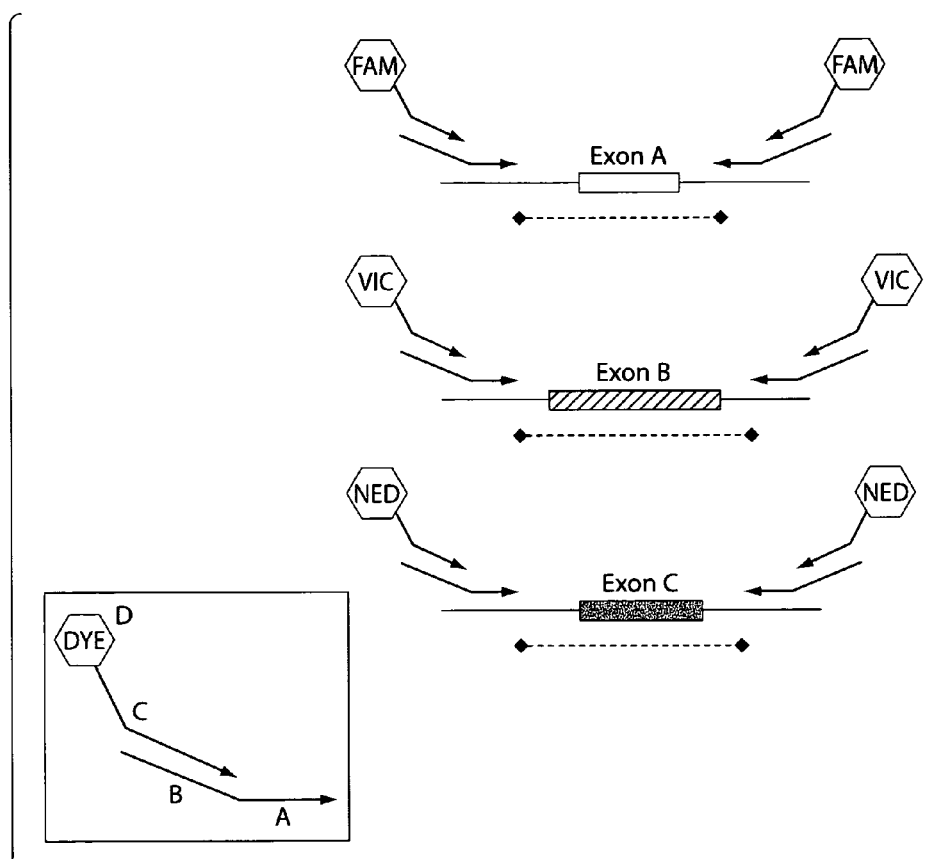
FIG. 2 depicts the amplification method. Primary amplification is performed with specific primers pairs that recognize sequences in introns around exons of interest (A) and tailed with either a forward or reverse tail sequence at the 3' end (B). Secondary amplification is performed with fluorescent universal secondary primers (C) with each of 3 possible flourophores (D: Fam, Vic or Ned). Variable amounts of intron sequence are used to control the length of the PCR product.

Each first primer contains a 5' region and a 3' region. The 3' region of the first primer is a PCR primer that is specific for the target nucleic acid sequence to be amplified. The 5' region of the first primer contains the "forward tail" a sequence that is identical across all first primers (FIG. 2, forward tail). It follows that the populations of all first primers share an identical forward tail (5' region, see, FIG. 2) and have different 3' regions each specific for a different target nucleic acid sequence in the nucleic acid sample.

The second primer is similar to the first primer. Each second primer contains a 5' region and a 3' region. The 3' region of the second primer is a PCR primer that is specific for the target nucleic acid sequence to be amplified. The 5' region of the second primer contains the "reverse tail" a sequence that is identical across all second primers (FIG. 2, reverse tail). It follows that the populations of all second primers share an identical reverse tail (5' region, see, FIG. 2) and have different 3' regions each specific for a different target nucleic acid sequence in the nucleic acid sample.

The amplified products generated from the plurality of target specific PCR primer pairs described above would have different lengths and different internal sequence but identical end sequences—a forward tail at one end and a reverse tail at the other end. In other words, one end of the amplified products would be identical to, or a compliment of, the 5' region of the first primer (FIG. 2, forward tail). The other end sequence would be identical to, or a compliment of, the 5' region of the second primer (FIG. 2, reverse tail). Because these amplified products have known end sequences, they can be uniformly amplified in a PCR reaction with known primers.

2b. Step (b)—Amplification of the Amplified Products

In step (b), the amplified products generated in the first step are further amplified. As discussed above, the amplified products generated in the first step all have identical end sequences—a forward tail at one end and a reverse tail at the other end. Since the amplified products have known end sequences, they can be amplified using a PCR reaction with amplified product specific primers.

Primers that may be used include: (1) a primer that comprise a 3' end that is identical to one portion of the forward tail and a primer that comprise a 3' end that is identical to one portion of the reverse tail and is labeled with a particular fluorescent molecule such as 6-FAM, Vic, Ned, Pet, etc. (2) a primer with the sequence of the forward tail and a primer with the sequence of the reverse tail and is labeled with a particular fluorescent molecule such as 6-FAM, Vic, Ned, Pet, etc. It is understood that the amplified product specific primers need not contain the complete sequence of the forward or reverse tail. Furthermore, the amplified product specific primers may contain additional 5' sequences.

It is understood that step (a) may be performed before step (b). For example, the multiplexed PCR of step (a) may be performed in a thermocycler. Following step (a) step (b) may be performed by the addition of amplified product specific primers to the reaction and initiating a second PCR reaction. Additional reagents, such as polymerase or dNTP may be added if needed. Additionally the amplified products may be mixed from individual PCR reactions preceding gel analysis.

It is also possible to perform the first step and the second step simultaneously by initiating a PCR with the nucleic acid sample, a plurality of target specific primer pairs, and the amplified product specific primer pair along with dNTP and polymerase. In this experimental setup, the initial rounds of PCR amplification will involve the target specific primers and the nucleic acid samples to generate amplified products. The amplified products are simultaneously amplified in a second PCR reaction within the same reaction chamber by the amplified product specific primers. In this way, the first and second steps can be performed simultaneously.

2c. Step (c)—Forming Homoduplexes and Heteroduplexes

In step (c), the amplified products generated by the first two steps are denatured and reannealed to form homoduplexes and, if there are sequence variations between the amplified products from one target nucleic acid primer pair, heteroduplexes.

One method of forming duplexes involves heating the amplified products until they are denatured and slowly reducing the temperature so that the denatured amplified products are reannealed. Another method involve heating the amplified products until they are denatured at 95° and the temperature decreased to 50° over 30 minutes If diploid genomic DNA is used as the target nucleic acid (the target nucleic acid) in a PCR reaction, the PCR reaction would be expected to amplify both alleles (copies) of the diploid DNA. If the PCR primers amplify a region of the diploid genome with no sequence differences, then the amplified products generated from the PCR would be expected to have the same sequence. In this case, heating and reannealing identical amplified products would be expected to generate homoduplexes and no heteroduplexes.

If the PCR primers amplify a region of the diploid genome with a sequence difference due to mutations, then two populations of amplified products would be produced. One population of amplified product would contain one variant of the nucleic acid sequence (e.g., the normal sequence) while the second population of amplified products would contain a second variant of the nucleic acid sequence (e.g., the mutant sequence). If the two populations of amplified products were heated and reannealed, four types of duplexes are expected to result as follows: (1) normal/normal duplexes, (2) normal/mutant duplexes, (3) mutant/normal duplexes, and (4) mutant/mutant duplexes (See, FIG. 1). The normal/normal duplexes and the mutant/mutant duplexes are homoduplexes (where both strands of the duplex have the same sequence) while the normal/mutant and mutant/normal duplexes are heteroduplexes.

2d. Step (d)—Detecting the Presence of the Heteroduplexes as Well as Mutant Homoduplexes as an Indicator of the One or More Sequence Changes.

As seen from the discussion above, heteroduplexes are only formed when there is a sequence difference among the amplified products generated by one target specific PCR primer pairs. Therefore, the existence of a heteroduplex is indicative of a sequence difference (e.g., mutation, insertion or deletion) between two copies of nucleic acids of a diploid genome. A mutant homoduplex also varies in mobility.

Heteroduplexes can be separated from homoduplexes and detected based on their physical characteristics because, unlike homoduplexes which are double stranded DNAs, heteroduplexes does not form perfect double stranded structures. Because of a region of noncomplementary DNA in its sequence, heteroduplexes can have one or more noncomplementary internal structures which cause a kink in the otherwise linear duplex DNA structure. Because of these structural differences, heteroduplexes and normal homoduplexes of the same length do not migrate at the same rate in a non-denaturing gel. Mutant homoduplexes are also altered in shape. This difference in migration rate can be made more apparent, for example, by the use of electrophoresis conditions that maximizes the differences between the homoduplex and heteroduplex structure, such as, for example, in a EGAN or confirmation sensitive electrophoresis gel (e.g., 1×MDE (1.13× MDE Gel Solution (Cambrex), 22.5% Formamide (Fisher Scientific), 15% Ethylene Glycol (Fisher Scientific), 0.05% ammonium persulfate (Fisher Scientific) and 0.005% N,N,N', N'-tetramethylethylenediamine (Fisher Scientific) in 0.6×TTE (44.4 mM Tris/14.25 mM Taurine/0.1 mM EDTA, pH 9.0)) which can separate homoduplexes and heteroduplexes based on their different migration rates under electrophoresis. Since the difference between the wild type homoduplexes, mutant homoduplexes and heteroduplexes are minor, they are still expected to migrate at slightly different rate in an EGAN gel and the heteroduplex band and the homoduplex bands are expected to be proximal to each other (See, FIG. 5).

Figure 5:
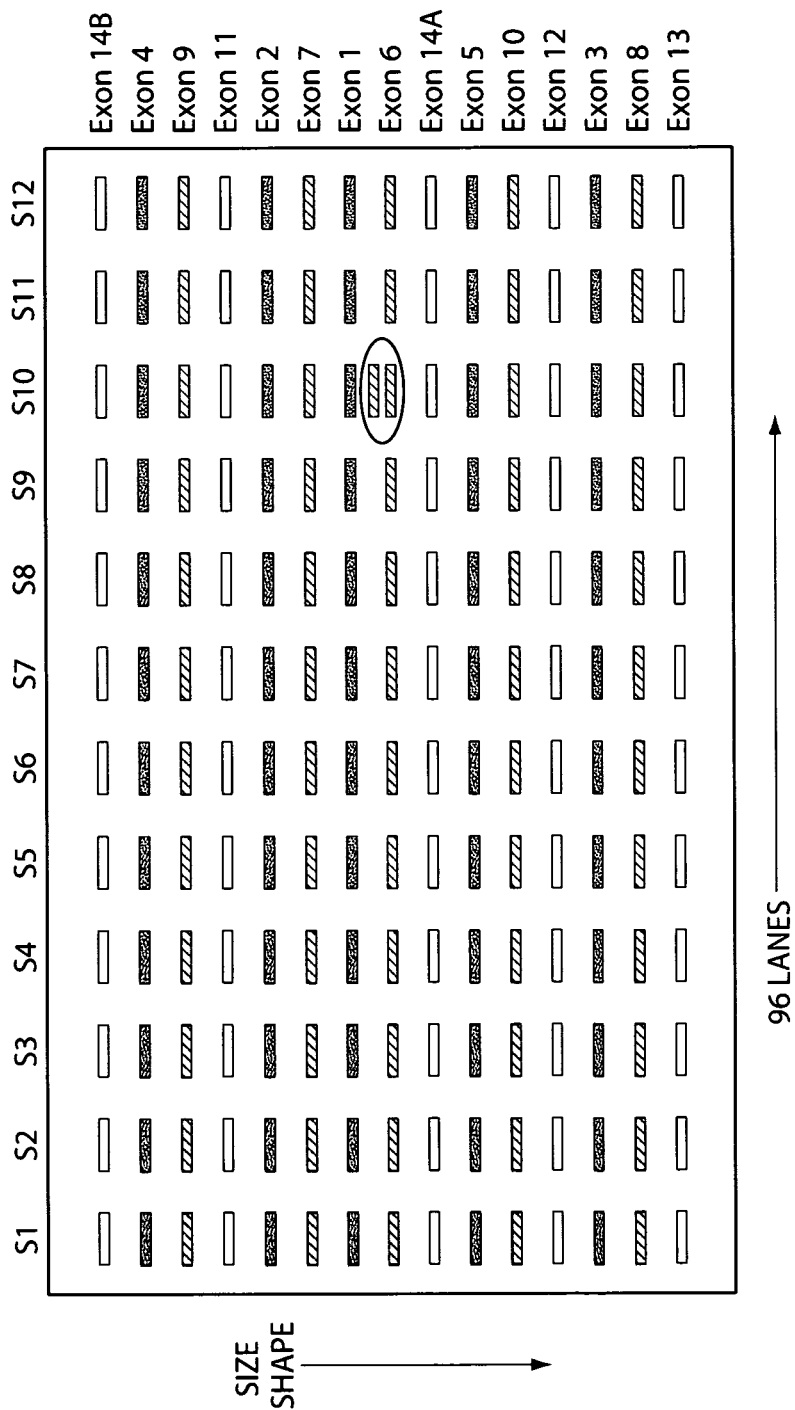
FIG. 5 is a schematic depiction of one method of nondenaturing analysis of amplified products. Homoduplexes and heteroduplexes generated from 96 separate patients (S1-S96) using 14 amplicons are mixed on a per patient basis and analyzed by Exon Grouping Analysis (EGAN) on a 96 gel lanes. A schematic of the first 12 lanes are shown. If no mutations are present, all the bands should contain the same homoduplexes and migrate at the same rate. Mutations present themselves as a mixture of homoduplexes and or heteroduplexes which have a different rate of migration due to alterations in DNA structure and which can be easily separated from the normal homoduplexes. See circled band corresponding to a mutation and its corresponding normal homoduplex in Patient S10.

Detecting the presence of a heteroduplex or mutant homoduplex may be performed, for example by EGAN analysis of the duplexes generated in step (c). FIG. 5 shows a schematic of an EGAN analysis of a plurality of reactions. Briefly, the methods of the invention are applied to a plurality of target nucleic acids in separate reactions to generate amplified products. The amplified products of each reaction are analyzed in separate lanes of an EGAN gel—which can be a confirmation sensitive electrophoresis gel.

Figure 6:
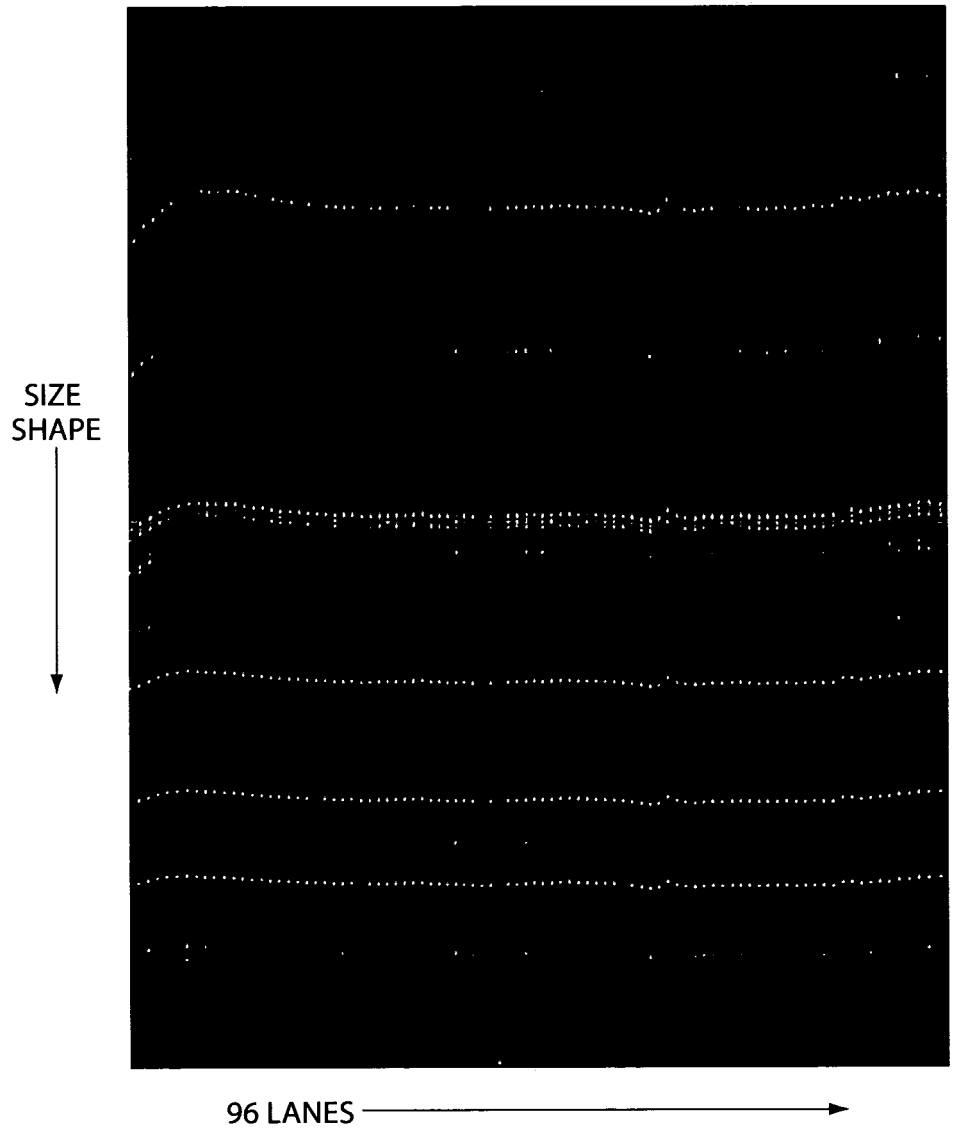
FIG. 6 is an actual Exon Grouping Analysis (EGAN) gel of homoduplexes and heteroduplexes represented schematically in FIG. 3. Note that the presence of the one mutation shown with the red circle will be the only fragment in the analysis requiring standard DNA sequencing as compared to the standard method which would have required sequencing of all 2400 exons analyzed on the gel. Moreover, since both forward and reverse sequencing on each of the exons would have been needed for a total of 4800 reactions Exon Grouping Analysis (EGAN) has increased throughput and reduced cost by a factor of about 5000.

Target nucleic acids with no mutations are expected to generate homoduplexes of the expected size. Target nucleic acids with mutations would generate homoduplexes or generate heteroduplexes (see FIG. 1). Under the appropriate electrophoresis conditions, the homoduplexes comprising different sequences and the heteroduplexes are expected to migrate at different rates forming distinct peaks—see, for example, the last scanned peak in FIG. 10 labeled 100%. In this panel, a mutant homodimer is shown in blue on top of a trace of a wildtype homodimer shown in grey. As shown clearly, the wildtype homodimers and mutant homodimers have different electrophoresis peaks. By scanning an EGAN gel by eye or by automated means (e.g., FIG. 5, FIG. 6), the presence of heteroduplexes, or mutant homoduplexes and hence mutations, are easily detected. FIG. 6 is an actual Exon Grouping Analysis (EGAN) gel of homoduplexes and heteroduplexes represented schematically in FIG. 3. Note that the presence of the one mutation shown with the red circle will be the only fragment in the analysis requiring standard DNA sequencing as compared to the standard method which would have required sequencing of all 2400 exons on the gel. Moreover, since both forward and reverse sequencing on each of the exons would have been needed for a total of 4800 reactions Exon Grouping Analysis (EGAN) has increased throughput and reduced cost by a factor of about 5000.

Figure 7:
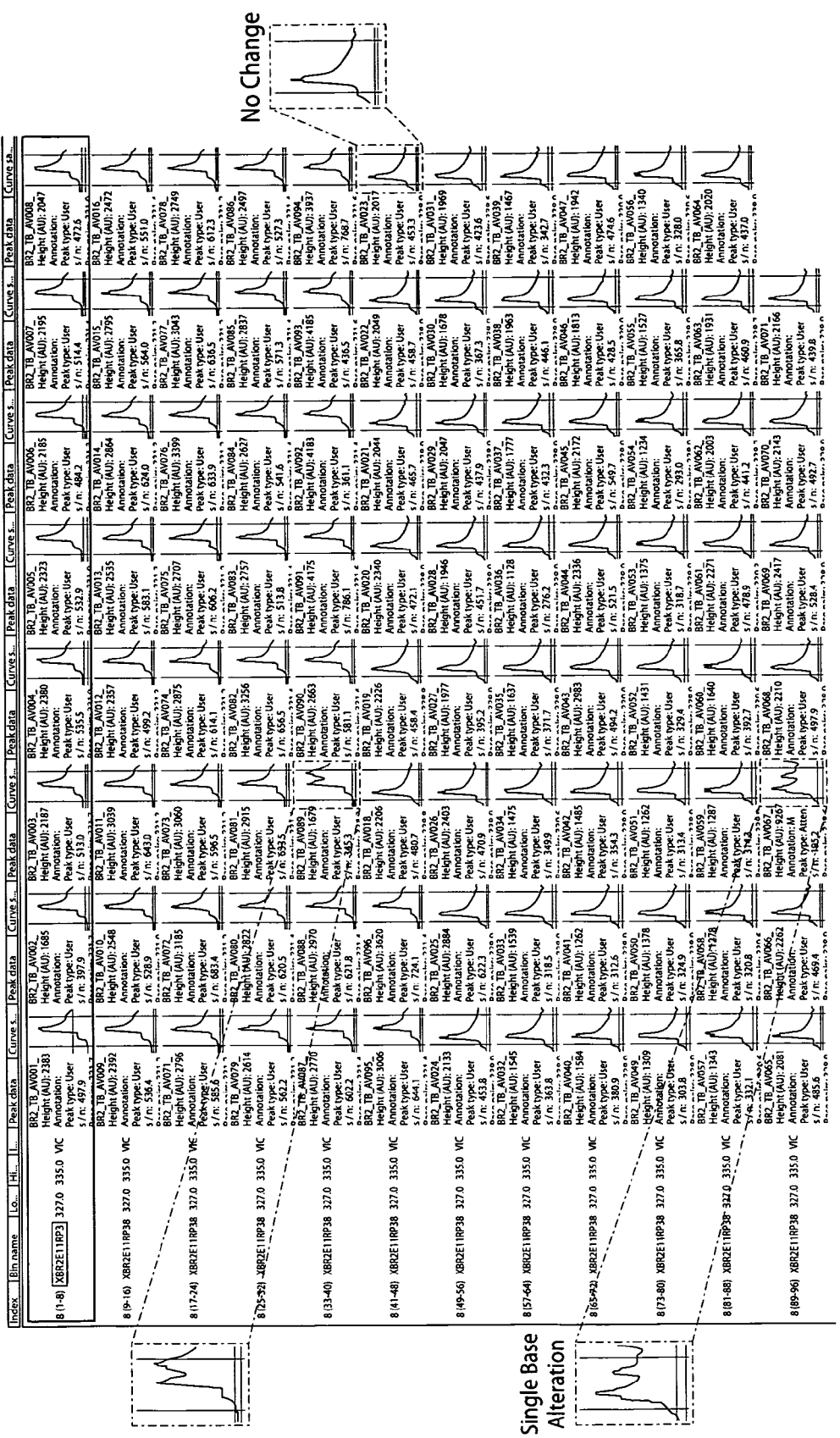
FIG. 7 depicts the output from analysis of one exon compared in 96 patients by the methods of the invention. The presence of a mutation causes a double peak at the position of mutation in 2 of 96 patients. These double peaks are magnified and highlighted in this figure. An example of the normal peak (labeled as "no change") is also magnified and highlighted.

The output of a scan of an electrophoresis gel designed to detect homoduplexes and heteroduplexes, referred to herein as a scan profile, are shown in FIG. 7. Each scan profile is calibrated to internal molecular weight standards embedded into each lane of a conformation sensitive electrophoresis gel. This enabled scan profiles obtained on different gels, different experiments and at different times to be compared to each other. As shown in the scan which is highlighted, a single base alteration is detectable as an altered profile in a scan. The altered profile represents peaks corresponding to the nucleic acid species such as allele A homodimers (e.g., wildtype homodimers), allele B homodimers (e.g., mutant homodimers) and allele A/allele B heterodimers (e.g., wildtype and mutation heterodimers).

Figure 8A:
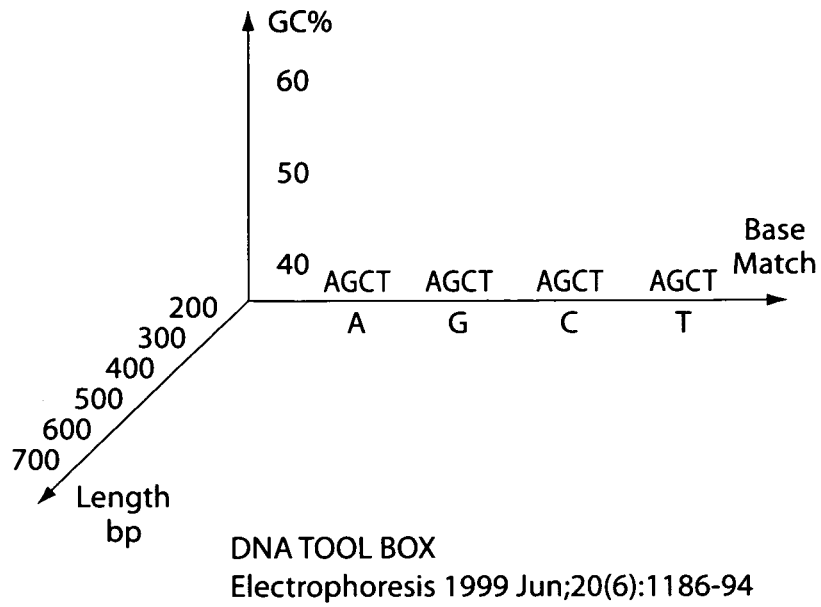
FIG. 8 depicts validation of Exon Grouping Analysis (EGAN) on a library of 216 distinct test amplicons. A. The amplified product range in size from 200 to 700 base pairs in the context of 40%, 50% and 60% GC richness. Each possible combination of GC richness and basepair length has a point mutation introduced where a base is changed to every other possible base. The invention was able to detect 214 of 216 possible changes for a sensitivity of 98%. B. An example is shown of the change in DNA shape as determined for the substitution of an A residue in a 40% GC rich fragment for either a G, C, or T residue. Note the specific alteration in shape for each possible substitution and the fact that each substitution leads to a different distinct shape.
Figure 8B:
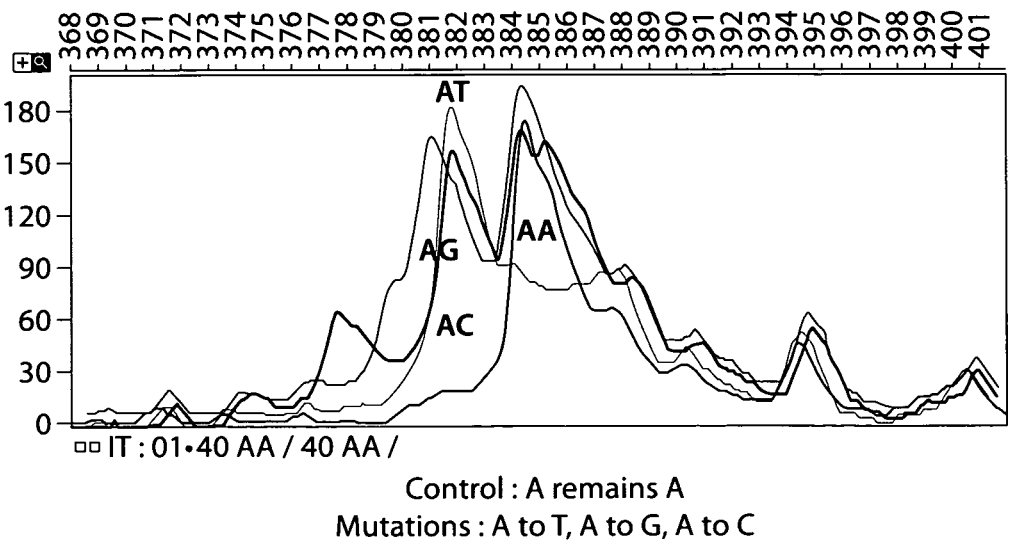

In an EGAN analysis, a mutation is expected to form three types of heterodimers. For example, if the wildtype sequence is an A, four types of mutations are possible (1) A to A, (2) A to C, (3) A to G and (4) A to T. The first mutation, A to A is silent and not distinguishable from an unmutated sequence (where A is unchanged). However, using the methods of the invention, the other three mutations produce distinct peaks which are distinguishable in a scan of an electrophoresis gel. One such gel scan is shown in FIG. 8B where each of the mutations caused a different peak on a gel scan. As shown in the Figure, The AA homodimer (in blue) shown a different peak profile from a AT heterodimer (in red), an AG heterodimer (in green) and an AC heterodimer (in black). The nature of the mutation (i.e., A to G, A to C, and A to T) may be determined by DNA sequencing and correlated to each different peak profiles. In subsequent analysis of the same DNA sequence, DNA sequencing is unnecessary because the nature of the mutation may be identified based on the previously identified peak profiles. It should be noted that conformation sensitive gel electrophoresis may substituted by other electrophoresis techniques such as capillary electrophoresis. For example, the capillaries are loaded with a combination of CAP polymer from ABI, TTE (Tris Taurine EDTA, previously described) and sucrose.

2e. Step (e)—Detecting The Mutation by Sequencing.

In an optional step, the nature of the mutation which caused the formation of the heteroduplexes, if any, may be determined. Since each amplified product of the reaction has a unique length and since the heteroduplexes migrate closely with the homoduplexes, the length of the heteroduplexes can be estimated. Based on the length of the heteroduplex, the identity of the PCR primers used can be determined.

Since the PCR primers sequences are known, the sequence of the heteroduplex may be determined by using the PCR primer as sequencing primers in a sequencing reaction. For example, the target nucleic acid may be amplified using the identified PCR primer pair to generate amplified products. The amplified products thus generated may be sequenced using one of the PCR primer pair.

The DNA sequencing may be performed manually or in an automated DNA sequencer. Since the heteroduplex contains a variation in at least one base, the sequencing of both variations using the PCR primer is expected to give rise to a double band, representing both versions of the DNA sequence, in one position. FIG. 11 shows the results of such an automated sequence output. As can be seen in FIG. 11, two bands are present at the mutation location. If desired, the sequencing reaction may be performed automatically and analyzed by computer.

3. Variations of EGAN

One advantage of EGAN is that multiple nucleic acid regions may be analyzed for mutations simultaneously. For example, all the exons of one or more oncogenes may be analyzed at the same time.

In one embodiment, EGAN may be performed with at least 5 primer pairs. Alternatively, the method may be performed using at least 10, at least 20, at least 30, at least 40, at least 50, or at least 80 primers pairs. The products of amplification reaction using these primer pairs may be analyzed in one lane of a EGAN gel. This is possible if each of the primers is labeled with a distinctive label. Further, in a preferred embodiment, each of the primer pairs may be designed to produce an amplified product of a distinct size. For example, one set of primers may produce an amplified DNA product of 300 bp, a second set of primers may produce an amplified DNA primer of 320 bp, a third set of primers may produce an amplified DNA primer of 340 bp and so on. Specific sized of amplified products may be produces for example, by including a variable amount of intron into the amplified product. Furthermore, a large exon may be targeted by two or more primer pairs for EGAN analysis. For example, an exon of 1000 bp may be targeted by primers which produce amplification products of 310 bps, 330 bps and 350 bps. Naturally, two or more closely spaced small exons may be analyzed as one amplified fragment. Further, two exons that are close together may be treated as one large exon for analysis. By including a variable amount of intronic sequence, by splitting a large exon into two or more amplification regions, and by treating two closely spaced exons as one large exon any gene, DNA region or RNA region, including whole genomes may be analyzed by the methods of the invention.

In another embodiment, first 5' region of the first target specific primer may be identical to the first 5' region of the second target specific primer. In other word, the forward tail and the reverse tail may have the same sequence (See, FIG. 2). Since the forward tail and reverse tail are identical, the amplified products generated would contain two identical end regions and these amplified products may be amplified in a PCR reaction with only one primer. Thus, in step (b), the amplified products may be further amplified using an oligonucleotide with the sequence of the forward tail.

One advantage to using identical forward tails and reverse tails is that the formation of primer dimers, a PCR artifact, is suppressed. Primer dimers are formed when two primers hybridize to each other in a PCR reaction and generate an amplified product comprising the sequence of both primers with no intervening sequence. Primer dimer formation introduces artifact amplified products into a PCR reaction and more importantly, reduce the signal and efficiency of PCR by consuming primers and dNTPs. It has been shown that primers with identical 5' regions (i.e., the forward tail is identical to the reverse tail, see FIG. 2), form primer dimers with complementary ends. In subsequent round of thermocycling, the primer dimers strands denature and anneal with itself forming panhandle structure which are resistant to further amplification because they self anneal and are resistant to hybridization to additional primers. See, Brownie, J., et al., Nucleic Acids Res. 25:3235-3241 (1997). Therefore, one additional benefit of using identical forward tails and reverse tails is the suppression of primer dimer formation.

In a preferred embodiment, one or more of any of the PCR primers of the invention may be labeled with a detectable label. The detectable label may comprise, for example, a fluorophore, an enzyme, a quencher, an enzyme inhibitor, a radioactive label, a member of a binding pair, and a combination thereof. Labeled primers facilitate the detection of the amplified products since the primers are incorporated into the amplified products during PCR. Alternatively, the amplification reaction may be performed in the presence of one or more labeled nucleotides (dNTPs) so that the amplified product is detectable. It is noted that not all the nucleotides needs to be labeled. For example, labeled amplified products can be produced if one, two, three, or all four of the dNTPs are labeled. Furthermore, only a fraction of any one dNTP is required to be labeled because an amplified product would contain more than one of any dNTP. So for example, an amplification reaction may be performed with dTTP, dGTP, dATP and dCTP where only 10% of the dTTP is labeled.

In another embodiment, EGAN may be used to monitor diseased tissue. In this method, nucleic acid extracted from diseased tissue (e.g., a tumor) and normal tissue may be used as starting material for EGAN. The homoduplexes and heteroduplexes generated from EGAN may be analyzed together to determine if a mutation is correlated with the diseased state. Preferably, the disease tissue and normal tissue are isolated from the same patient The oligonucleotides used in this disclosure, including the various PCR primers, may be synthesized chemically by methods that are standard in the art, e.g. using commercially available automated synthesizers. Synthesized oligonucleotides may be labeled with a detectable label. For example, fluorochromes (such as FITC or rhodamine), enzymes (such as alkaline phosphatase), biotin, radioactive compounds, or other well-known labeling compounds may be attached directly or indirectly.

The present invention accommodates the simultaneous screening of a large number of potential target nucleic acids (mutation locations) in a single reaction. In practice, the actual number of target nucleic acids that are amplified for simultaneous analysis may be determined according to the diagnostic need. For example, breast cancer biopsies may be analyzed by targeting BRCA1 and BRCA2 exons. Sickle cell anemia patients may be analyzed by targeting β-globin exons.

The method of the invention may be used to detect base changes in expressed DNA and unexpressed DNA (e.g., mutations in regulatory regions) resulting from a mutation, insertion, deletion of one or more bases.

The method of the invention may be used to detection mutations in any type of cell in which nucleic acid material can be extracted. These include eukaryotic cells, prokaryotic cells, and plant cells. Furthermore, analysis is not limited to genomic DNA, mitochondrial DNA, mRNA, ribosomal RNA and structural RNA mutations may be analyzed by the methods of the invention.

By using cells in different stages of development, differentiation, malignant transformation etc, and appropriate references cells, it is possible to detect base changes underlying the transition from one cell phenotype to another, for example, detecting base changes associated with a particular disease or disorder, developmental processes, etc.

Since prior knowledge of the mutation is not necessary for detection of mutations, the methods of the invention may be used to identify novel mutations in various processes of disease, differentiation and development.

The method of the invention can be used to detect base changes in DNA after treatment in vitro or in vivo of cells or whole organisms with physical (x-ray, uv irradiation, atomic particle bombardment etc), chemical (drugs, various compounds, biological products, etc) or biological (viruses, bacteria, etc) agents. In another aspect, the method of the invention may be used to study DNA polymorphic differences among individuals, and populations for example, in determining risk for certain diseases etc. Further, the method of the invention may be used to study DNA mutations and variations in the process of aging (e.g., loss of telomeres, accumulation of mutations).

The following examples are intended to further illustrate the present invention without limiting the invention thereof.

EXAMPLES

Example 1

Amplification of Target DNA and the Formation of Homoduplexes and Heteroduplexes A) Preparation of Sample DNA from Blood DNA may be collected from blood. White blood cells collected from the peripheral blood were lysed with two washes of a 10:1 (v/v) mixture of 14 mM $NH_4Cl$ and 1 mM $NaHCO_3$. The nuclei were resuspended in nuclei-lysis buffer (10 mM Tris, pH 8.0, 0.4M NaCl, 2 mM EDTA, 0.5% SDS, 500 ug/ml proteinase K) and incubated overnight at 37° C. Samples were then extracted with a one-fourth volume of saturated NaCl and the DNA was precipitated in ethanol. The DNA was then washed with 70% ethanol, dried, and dissolved in TE buffer (10 mM Tris-HCl, pH 7.5, 1 mM EDTA.). Ninety-five DNA samples from breast cancer patients and controls were obtained at DFCI under IRB approved protocols.

Primers for 88 PCR fragments (34 BRCA1 and 54 BRCA2) were chosen to span the coding region of BRCA1 and BRCA2. The PCR fragments ranged from 232 to 558 base pairs in BRCA1 and 194 to 567 base pairs in BRCA2. Large exons, BRCA1 exon 11 and BRCA2 exons 10, 11, 14, 18 and 27, were amplified in several overlapping fragments. Each PCR fragment was labeled with a FAM, VIC, or NED fluorescent primer by a secondary PCR amplification and organized into 5 multiplexed PCR lanes, 2 lanes for BRCA1 and 3 for BRCA2. The multiplexed PCR groups were organized to maximize base pair separation between primers labeled in the same color. DNA samples were arranged in 96 well format. All reactions were prepared using a 96 channel Tecan Genmate robotic system.

The primary reactions were carried out in a final volume of 4 μL containing 4 ηg of genomic DNA; primers at a concentration of 0.2 μM; HotstarTaq DNA Polymerase (Qiagen) at 1× concentration. All forward primers contained the following sequence tail, 5'-GCGTACTAGCGTACCACGTGTC-GACT-3' (SEQ ID NO:1). All reverse primers contained the following sequence tail, 5'-GACGATACGACGGGCGTAC-TAGCGTA-3' (SEQ ID NO:2).

Thermocycling conditions were performed in a Geneamp PCR system 9700 (Applied Biosystems): The PCR amplification conditions consisted of an initial denaturation step at 95° C. for 15 minutes followed by 30 cycles of denaturation at 95° C. for 30 s, annealing at 60° C. for 45 s, and extension at 68.5° C. for 60 s. The annealing temperature was decreased by 0.5° C. in each cycle until a final annealing temperature of 45° C. was reached. Finally, 15 cycles of denaturation at 95° C. for 30 s, annealing at 45° C. for 45 s, and extension at 68.5° C. for 60 s and a final extension at 68.5° C. for 10 minutes.

The secondary PCR reactions were performed in a final volume of 4.5 μL of 1× HotstarTaq DNA Polymerase with FAM, VIC or NED fluorescently labeled forward and reverse primers at a concentration of 0.2 μM. The primary PCR amplification was tip-touched into the fluorescently labeled 1× HotstarTaq solution using the Genmate robot.

Thermocycling conditions for the secondary amplification consisted of an initial denaturation step at 95° C. for 15 minutes followed by 25 cycles at 94° C. for 30 s, annealing at 56° C. for 45 s, and extension at 68.5° C. for 60 s and a final extension step at 72° C. for 10 minutes. The heteroduplex formation step was performed after the final extension by heating the samples to 96° C. then decreasing the temperature by 4 degrees every 3 minutes to 56° C. and then cooled to 4° C.

Example 2

Analysis of Amplified DNA by Electrophoresis and DNA Sequencing

Multiplexed PCR Lanes

The 5 multiplexed PCR lanes consist of 6 FAM-labeled primers, 6 VIC-labeled primers and 6 NED-labeled primers. Following the heteroduplex formation, primers labeled in the same color from each patient are mixed together in 25 μL of PCR buffer (0.05M Tris, 0.05M KCL, pH 8.0). These multiplexed PCR fragments are then combined in a 3 FAM: 4 VIC: 6 NED ratio. The approximate final dilutions of PCR product are as follows: 1:100 FAM; 1:70 VIC; 1:45 NED. Finally the FAM, VIC, NED multiplexed mixture is combined in a 1:1 ratio with our ROX labeled size standard.

Scanning of Multiplexed PCR Products

The 0.2-mm thick gel was prepared with 1.13×MDE Gel Solution (Cambrex), 22.5% Formamide (Fisher Scientific), 15% Ethylene Glycol (Fisher Scientific), 0.05% ammonium persulfate (Fisher Scientific) and 0.005% N,N,N', N'tetramethylethylenediamine (Fisher Scientific) in 0.6×TTE (44.4 mM Tris/14.25 mM Taurine/0.1 mM EDTA, pH 9.0). The optimal polymerization time for the gel was approximately 45 minutes. Allowing the gel to polymerize for too long results in the gel drying out and the formation of "red rain". 0.5 μL of the PCR product/ROX size standard mixture was loaded onto the 96 lane comb (The Gel Company) by 6× loading using the Matrix Impact 8-channel pipette. Electrophoresis of the multiplexed PCR fragments using 0.6×TTE as the electrode buffer was performed using an ABI 377 DNA sequencer. Using an external cooling system, the samples were electrophoresed at 18° C. using power as the limiting factor set at 40 W and a run time of 22 hours.

Molecular weight markers were used in each gel lane to calibrate the size of the analyte. Briefly, a total of eighteen molecular weight markers, each labeled with a ROX fluorophore, were added to each sample. These molecular weight markers were: (1) 160, (2) 182, (3) 201, (4) 227, (5) 254, (6) 272, (7) 306, (8) 337, (9) 362, (10) 400, (11) 425, (12) 459, (13) 486, (14) 509, (15) 551, (16) 560, (17) 598, and (18) 613. The scanned peaks of each homodimer and/or heterodimer are represented as migration speed relative to these molecular weight markers.]

Sequencing

Fragments exhibiting an altered pattern were re-amplified by cherry picking the appropriate DNA and primer combination using a Tecan Genesis robot. The primary reaction conditions were identical to the conditions used in the primary reactions used in the EGAN protocol. The primers were as follows:

T7 Pigtails:
5'-GTAATACGACTCACTATAGGGCGTAC-TAGCGTACCACGTGT-3'(SEQ ID NO:3) T3 Pigtails:
5'-GATTAACCCTCACTAAAGGGAGAC-GATACGACGGGCGTACTA-3'(SEQ ID NO:4) These primers were incorporated in each fragment by a secondary amplification. A 10 µL reaction containing 1× HotstarTaq with 0.2 µM T7/T3 pigtail primers was set-up by transferring 0.1 ul of the primary reaction using a disposable 96 pin transfer tool (V&P Scientific, Inc., San Diego, Calif.) into the secondary reaction containing all the components. Thermocycling conditions for the secondary amplification consisted of an initial denaturation step at 95° C. for 15 minutes followed by 25 cycles at 94° C. for 30 s, annealing at 60° C. for 45 s, and extension at 68.5° C. for 60 s and a final extension step at 72° C. for 10 minutes. PCR products were cleaned using the AMPure (Agencourt) protocol. The cleaned PCR products were eluted in 30 µL of 10 mM Tris pH 8.0.

The BigDye sequencing mixture consisted of a 1:5 solution of ABI BigDye and Better buffer (The Gel Company) with 1.6 µM T7 sequencing primer (5'-TAATACGACTCACTAT-AGGG-3') (SEQ ID NO:5) or 1.6 µMT3 sequencing primer (5'-ATTAACCCTCACTAAAGGGA-3') (SEQ ID NO:6). For each PCR fragment a 4 µL reaction (1:1 mixture of BigDye and PCR fragment) was prepared for the forward (T7) and reverse (T3) sequences. The ABI BigDye thermocycling conditions were used for the sequencing reaction. Sequencing reaction clean up was done according to the CleanSeq (commercially available from Agencourt Bioscience Corporation, Beverly, Mass.) protocol. Samples were eluted in water. Analysis was preformed using an ABI 3730 DNA sequencer.

Example 3

Validation of Exon Grouping Analysis

Exon Grouping Analysis (EGAN) on a library of 216 distinct test amplicons were tested and validated. For testing and evaluation, amplicons of different characteristics were tested. These characteristics includes size, GC richness (which can be expressed as % GC, % pyrimidines or % purines), and the nature of mutation. The nature of mutation may be the change of any one base of a nucleic acid sequence to any other base. A total of 12 types of mutations, such as A to G, A to C, A to T, G to A, G to T, G to C, C to G, C to T, C to A, or T to A, T to G, and T to C, can occur. Of course, point mutations that do not alter sequence, such as A to A, G to G, C to C and T to T are not detected. These parameters are plotted in FIG. 8A. In FIG. 8A, the amplicons range in size from 200 to 700 base pairs in the context of 40%, 50% and 60% GC richness. Each possible combination of GC richness and basepair length has a point mutation introduced where a base is changed to every other possible base.

The tests were performed as follows. Briefly, amplicons with different mutations were produced by PCR. These amplicons range in size from 200 to 700 base pairs and in GC richness (% GC) from 40 to 60%. Briefly, the tests were performed as follows. Amlicons were prepared from plasmids of varying GC richness and engineered point mutations as described in (Electrophoresis 20(6):1186-94). The products were mixed according to size and analyzed using the EGAN process.

The invention was able to detect 214 of 216 possible changes for a sensitivity of 98%. An example of one change detected by the methods of the invention is shown in FIG. 8B. In this figure, an example is shown of the change in DNA shape as determined for the substitution of an A residue in a 40% GC rich fragment for either a G, C, or T residue. Surprisingly, we found that there is a specific alteration in shape for each possible substitution. That is, each substitution produces a distinct peak shape for the heteroduplex migration on a gel. For example, an A to G substitution produces a different shape than an A to T substitution and which is also different from an A to C substitution. Based on this, once a substitution profile is known for one mutation location, it is possible to determine the nature of the substitution in future experiments (i.e., A to G, A to C, or A to T) without having to sequence the heteroduplex. That is because each substitution produces a unique shape on a densitomer scan of the homoduplex gel.

More surprisingly, it was found that heteroduplexes and homoduplex with different point mutations also have different peaks shapes. That is, each of the following structures would have a different migration rate.

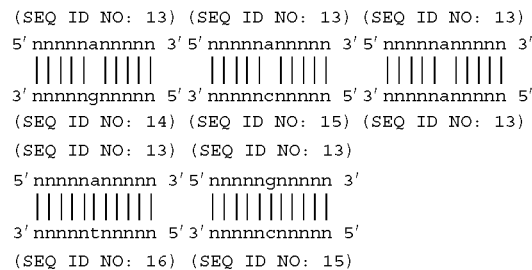

(where nnnnn represents 5' and 3' sequences which are identical for the example above and the total size of the heteroduplexes is between 200 to 700 basepairs in length).

The methods of the invention, because of its ability to differentiate between homoduplexes of different sequences, may be used to monitor gene conversion events and loss of heterozygosity events that are associated with some forms of disorders.

In another experiment to determine the sensitivity of the exon grouping analysis, we used two plasmids to test the sensitivity of the assay in a setting that mimics conditions that would be seen in an analysis where the tumor allele represents a minority of the total DNA. Such a possibility may be seen, for example, in a tumor biopsy where a tumor that is infiltrated with lymphocytes and other normal cells which do not carry the mutation that caused the cancer. Furthermore, this possibility is also possible where a sample being analyzed (e.g., such as a tumor biopsy or a blood sample containing cancerous mononuclear cells) contains a mixture of tumor and normal cells.

Figure 9A:
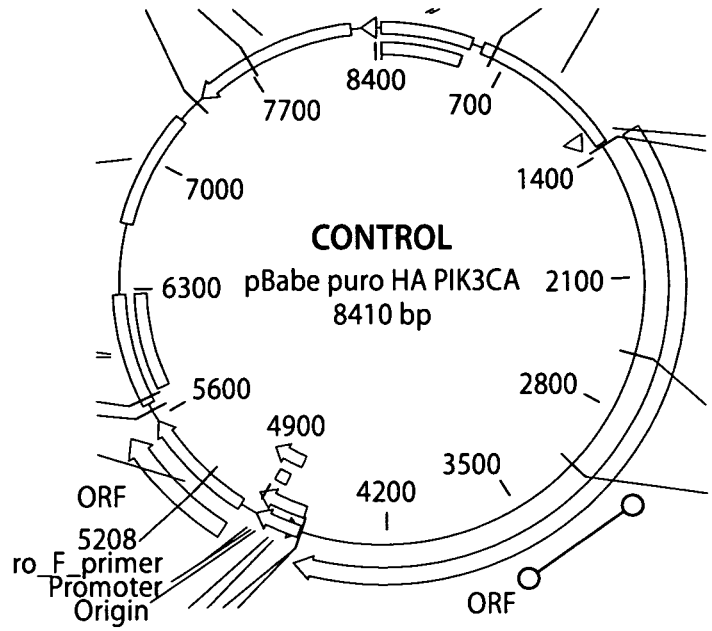
FIG. 9 depicts the plasmids used to test the sensitivity of the invention in a setting where the tumor allele represents a minority of the total DNA such as in a tumor that is infiltrated with lymphocytes and other normal cells. A. depicts a vector containing the cDNA for the PIK3CA gene (shown in blue). The region of interest that is amplified in the test is shown in gray. B. The same construct as in A. is shown with the single base lesion leading to the well characterized tumor change H1047R. By mixing the plasmids in various ratios of mutant to wild-type one mimics variable content of mutant DNA in a tumor.
Figure 9B:
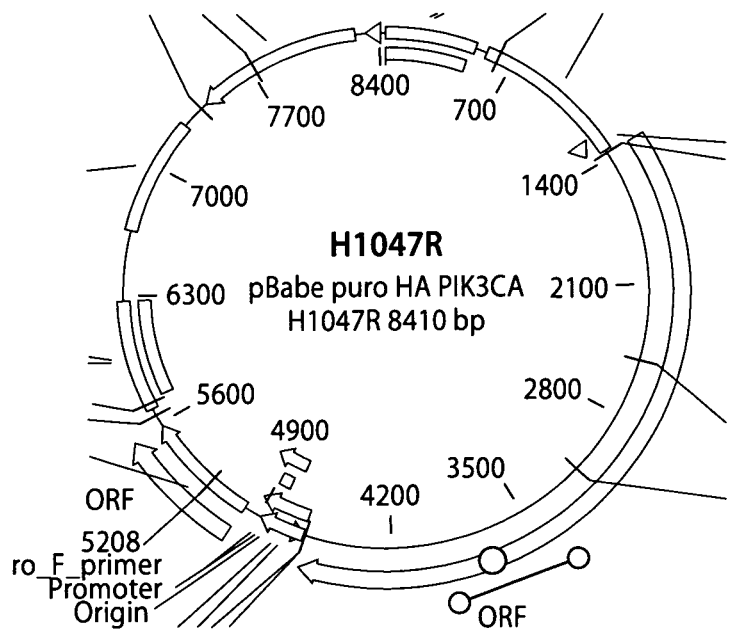

The two plasmids are depicted in FIG. 9. In this figure, panel A depicts a vector containing the cDNA for the normal (nonmutant) PIK3CA gene (shown in blue). The region of interest that is amplified in the test is shown in gray. Panel B depicts the same construct as in A but with the single base lesion leading to the well characterized tumor change H1047R. By mixing the plasmids in various ratios of mutant to wild-type one mimics variable content of mutant DNA in a tumor. For example, in FIG. 10, the ratio of normal to mutant (control plasmid to H1047R plasmid, see FIG. 9) are mixed in ratios of 0%, 2%, 4%, 6%, 8%, 10%, 12%, 14%, 16%, 18%, 20%, 30%, 40%, 50%, 60%, 70%, 80%, 82%, 84%, 86%, 88%, 90%, 92%, 94%, 96%, 98%, and 100%. Briefly, 0% represents 100% control plasmid and 0% H1047R plasmid; 6% represents 94% control plasmid and 6% H1047R plasmid; and 100% represents 0% control plasmid and 100% H1047R plasmid. The plasmids were mixed according to concentration to result in the ratios described above. PCR amlicons using the mixture as the template with primers surrounding the mutations were analyzed on EGAN gels.

Figure 10:
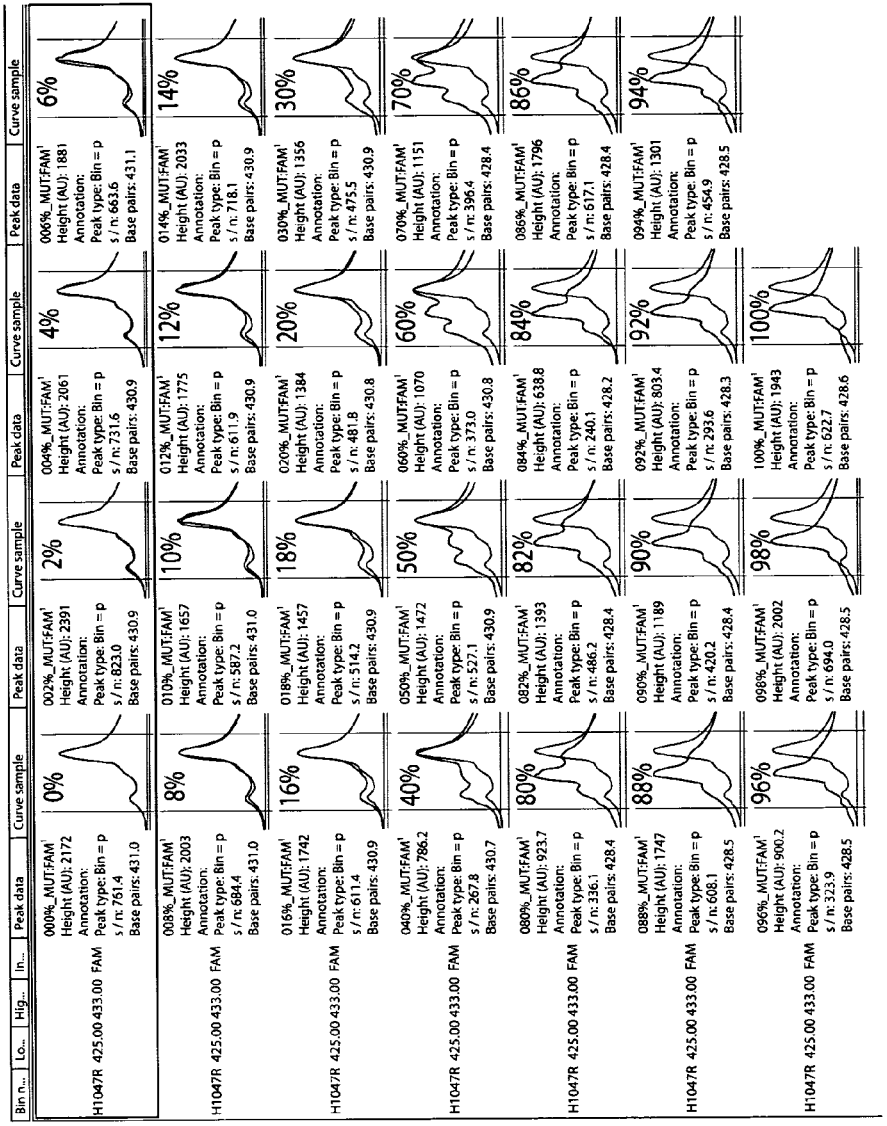
FIG. 10 depicts the results of the invention analysis of a range of tumor purity as measured by PCR amplification of various ratios of mutant and normal PIK3CA genes. The results of the shape changes induced by the mutant are depicted in blue (lighter shaded line in a grayscale Figure) and are superimposed on the 0% tumor control in gray (darker shaded line in a grayscale Figure). A change in the shape pattern is obvious at a tumor purity of 6% (note the divergence in the shape of the mutant in blue as compared to the normal in gray on the 4$^{th}$ panel in the first row. It is important to note that even though the 100% tumor band is composed of a homodimer (mutant sequences) it is clearly different in shape as compared to the normal control which is also a homodimer (normal sequences). This shows the sensitivity of EGAN in a context of either low tumor purity or in a situation when the normal allele is lost in the tumor (loss of heterozygosity).

In FIG. 10, the results of the shape changes induced by the mutant are depicted in blue and are superimposed on the 0% tumor control in gray. Each chart in FIG. 10 represents a conformation sensitive gel electrophoresis of a homodimer/heteroduplex formed using the methods of the invention as described in the previous examples. The peaks were normalized to at least three molecular weight standards which were each fluorescently labeled.

As shown in FIG. 10, a change in the shape pattern is obvious when at least 6% of the sample being tested contain a different sequence (capable of heteroduplex formation). Thus, at a tumor purity of 6% or 94% (note the divergence in the shape of the mutant in blue as compared to the normal in gray on the 6% pattern and the 94% pattern.

Furthermore, it is noted that even though the 100% tumor band is composed of a homodimer (mutant sequences) it is clearly different in shape as compared to the normal control which is also a homodimer (normal sequences). This shows the sensitivity of EGAN in a context of either low tumor purity or in a situation when the normal allele is lost in the tumor (loss of heterozygosity).

Example 4

Validation of Exon Grouping Analysis Using Tumor Samples

We performed additional experiments to determine if Exon Grouping Analysis is capable of detecting mutations in actual tumors. Mutation detection in actual tumors is technically more challenging because of the presence of unrelated genomic DNA from normal tissue and unrelated DNA from other chromosomes with do not carry the mutation of interest.

Briefly, the reaction conditions were as follows:

DNA was extracted from bulk, fresh frozen tumors using standard DNA preparation kits (Qiagen, Inc.). Intronic primers were used to amplify the region of interest using the procedures described above.

Figure 11A:
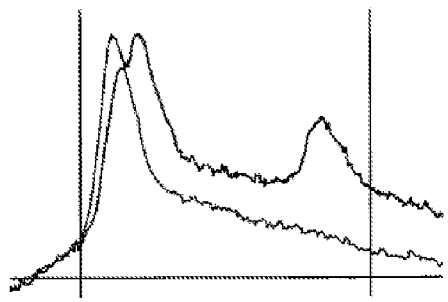
FIG. 11 depicts the EGAN analysis off DNA material from an actual breast cancer tumor. A. the actual alteration in the EGAN shape of the G1047R (in blue) compared to the normal control (in gray). B. depicts the standard sequencing of the same tumor DNA.
Figure 11B:
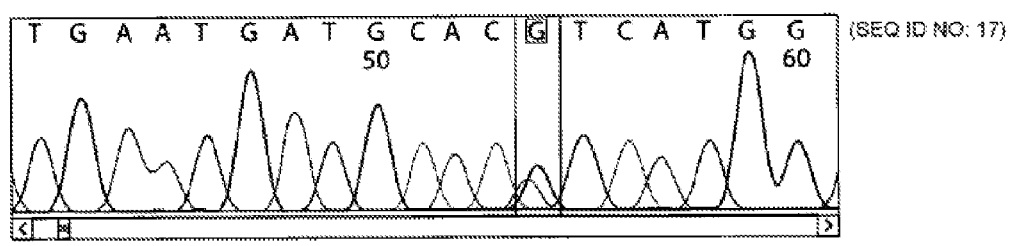

As shown in FIG. 11A, the actual alteration in the EGAN shape of the G1047R (in blue) compared to the normal control (in gray) was detectable even when the starting material used was a tumor biopsy. Furthermore, FIG. 11B shows the expected mutation that could be predicted from the EGAN analysis when the DNA was sequenced. See, the highlighted region of FIG. 11B where the mutation is highlighted.

Example 5

Validation of Exon Grouping Analysis (EGAN) to Detect BRCA1 and BRCA2

A validation study was conducted of the EGAN methodology applied to BRCA1 and BRCA2 analysis in a blinded set of 95 patients with clinical sequencing results. 88 amplicons were batched for BRCA1 and BRCA2 analysis on 5 gel lanes. Visual inspection of 8,360 EGAN peaks resulted in selection of 150 amplicons for sequencing resulting in a cost savings of 98.2% over direct sequencing alone. There were a total of 64 clinically reportable alterations in this set of patients. 2 large indels were not identifiable by either technique. A nonsense mutation was missed by EGAN and an uncharacterized variant not reported following clinical sequencing. The sensitivities of both procedures are equivalent with 61 of 62 possible alterations detected for an overall sensitivity of 98.4%. Receiver Operator Curve analysis of automatic peak analysis algorithms developed in the study identified mutant amplicons with very good sensitivity and specificity with area under the curve (AUC) of 0.994. EGAN detects insertions, deletions and single base alterations with the same sensitivity as sequencing. The EGAN process is a sensitive, specific, high throughput, rapid and inexpensive mutation detection workflow that can be applied to any gene of interest.

General Methods

Patient Cohort and Sample Handling:

Ninety-five DNA samples consisting of a combination of breast cancer patients and controls were obtained at DFCI under IRB approved protocols (#93-085). Patient identifier information was coded and not made available to the laboratory. The blinded set of DNA samples was provided to the laboratory and coded internally.

Primer Picking Methodology:

BRCA1 and BRCA2 primers were picked using software designed in house based on iterative use of Primer3, a widely used program for designing PCR primers {Rozen, 2000 #1}. Primer3 uses input parameters, which control the characteristics of the primers and resulting PCR products. The algorithm imports the gene's genomic DNA sequence from the NCBI website (GenBank), extracts its mRNA and coding exon information and parses them to Primer3 in an iterative fashion. The output primers from Primer3 are monitored to ensure appropriate size range and distribution.

The specific methodology employed is: First, large exons (more than 450 bps) broken down into smaller fragments before primer design; second, size slots created from 200 to 500 bps, with ~50 as the interval. Each time after Primer Pick obtains the output from Primer3, it attempts to fill the matching size slots. For those products that don't fit, Primer Pick expands or further breaks down the target exons and submits them to primer3 iteratively. The program also bypasses the 20,000 base limitation of Primer3 by breaking down any larger regions initially. Large exons are covered with overlapping PCR products and smaller exons are amplified with primers in the surrounding intronic sequence.

DNA Amplification:

The primary reactions were carried out in a final volume of 4 µL containing 4 ηg of genomic DNA; primers at a concentration of 0.2 µM; HotstarTaq DNA Polymerase (Qiagen) at 1× concentration. All forward primers contained the following sequence tail, 5'-GCGTACTAGCGTACCACGTGTC-GACT-3' (SEQ ID NO:7) [1]. All reverse primers contained the following sequence tail, 5'-GACGATACGACGGGCG-TACTAGCGTA-3'(SEQ ID NO:8) [1].

Thermocycling conditions were performed in a Geneamp PCR system 9700 (Applied Biosystems): The PCR amplification conditions consisted of an initial denaturation step at 95° C. for 15 minutes followed by 30 cycles of denaturation at 95° C. for 30 s, annealing at 60° C. for 45 s, and extension at 68.5° C. for 60 s. The annealing temperature was decreased by 0.5° C. in each cycle until a final annealing temperature of 45° C. was reached. Finally, 15 cycles of denaturation at 95° C. for 30 s, annealing at 45° C. for 45 s, and extension at 68.5° C. for 60 s and a final extension at 68.5° C. for 10 minutes.

The secondary PCR reactions were performed in a final volume of 4.5 µL of 1× HotstarTaq DNA Polymerase with FAM, VIC or NED fluorescently labeled forward and reverse primers at a concentration of 0.2 µM. The primary PCR amplification was tip-touched into the fluorescently labeled 1× HotstarTaq solution using the Genmate robot.

Thermocycling conditions for the secondary amplification consisted of an initial denaturation step at 95° C. for 15 minutes followed by 25 cycles at 94° C. for 30 s, annealing at 56° C. for 45 s, and extension at 68.5° C. for 60 s and a final extension step at 72° C. for 10 minutes. The heteroduplex formation step was performed after the final extension by heating the samples to 96° C. then decreasing the temperature by 4 degrees every 3 minutes to 56° C. and then cooled to 4° C.

Post-PCR Multiplexing:

The 5 multiplexed PCR lanes (2 for BRCA1 and 3 for BRCA2) consist of 6 FAM-labeled primers, 6 VIC-labeled primers and 6 NED-labeled primers. Following the heteroduplex formation, primers labeled in the same color from each patient are mixed together in 25 µL of PCR buffer (0.05M Tris, 0.05M KCL, pH 8.0). These multiplexed PCR fragments are then combined in a 3 FAM: 4 VIC: 6 NED ratio. The approximate final dilutions of PCR product are as follows: 1:100 FAM; 1:70 VIC; 1:45 NED. Finally the FAM, VIC, NED multiplexed mixture is combined in a 1:1 ratio with our ROX labeled size standard.

Scanning of Multiplexed PCR Products:

The 0.2-mm thick gel for the ABI377 was prepared with 1.13×MDE Gel Solution (Cambrex), 22.5% Formamide (Fisher Scientific), 15% Ethylene Glycol (Fisher Scientific), 0.05% ammonium persulfate (Fisher Scientific) and 0.005% N,N,N',N'-tetramethylethylenediamine (Fisher Scientific) in 0.6×TTE (44.4 mM Tris/14.25 mM Taurine/0.1 mM EDTA, pH 9.0). The optimal polymerization time for the gel was approximately 45 minutes. Allowing the gel to polymerize for too long results in the gel drying out and the formation of "red rain". 0.5 µL of the PCR product/ROX size standard mixture was loaded onto the 96 lane comb (The Gel Company) by 6× loading using the Matrix Impact 8-channel pipette. Electrophoresis of the multiplexed PCR fragments using 0.6×TTE as the electrode buffer was performed using an ABI 377 DNA sequencer. Using an external cooling system, the samples were electrophoresed at 18° C. using power as the limiting factor set at 40 W and a run time of 22 hours. Rox labeled molecular weight markers were used in each gel lane as internal standards (The Gel Company).

Export and Initial Analysis of GEL Data:

Raw data from the ABI 377 (Applied Biosystems, CA) was exported as .FSA files for each lane. The files were the imported to the Data Acquisition and Data Analysis (DAx) software package (Van Mierlo Software Consultancy, Eindhoven, The Netherlands). DAx was used to construct and subtract baselines, convert the x-axis from migration time to base pair size, identify peaks, normalize and place peaks in individual bins. Bin sizes were designed to include a single PCR product as well as cover half the distance between the next smaller and the next larger product. The data from each bin which represents an x-y matrix of mobility versus peak height for each PCR fragment in each of 95 patients was exported as a text file. The file also includes information on signal to noise ratios for each peak.

Noise Filtering:

After gel analysis, bands may lack sufficient signal strength to be discriminated from background noise. DAx software reports a signal-to-noise log ratio for each band curve. Curves with either a negative signal-to-noise log ratio or maximum height less than a certain threshold H, are removed prior to any calculation. Furthermore, some curves have such a strong signal that reaches a saturated level around the peak location. This saturation problem may increase the variance of curves from the same probe set and thus reduce the sensitivity of mutation detection. Although it is possible to predict saturated curves, it is easier to simply remove curves with maximum height above a threshold $H_h$ before any calculation. In this paper, we set $H_l=100$ and $H_h=6000$.

Shift Correlation:

Correlation is widely used as a similarity measure between two samples. Compared to Euclidean distance, correlation is more tolerant to x-axis shifting, such as latency effect in time series data. For the band curves from the polyacrylamide gel experiment, data from different gels are put together and compared. The x-axis shifting is necessary to compare the curves because the curves can not be aligned perfectly. One possible solution to remove this shifting effect is to find the best multiple alignment of the curves. However, because each gel has an individual shape morphing effect, a multiple alignment solution does not necessarily provide the best pairwise alignments and is relatively time-consuming. Here a pairwise alignment approach was adopted to remove the horizontal shifting effect and provide similarity measurement to each pair of curves. This measure is called "shift correlation". For two curve $X_1$ and $X_2$, each with total T data points, and a shift range $[-s, s]$ ($s>0$), their shift correlation $c_s(X_1, X_2)$ is defined as $$c_s(X_1, X_2) = \max_{-s \le l \le s} cor_l(X_1, X_2),$$

$$cor_l(X_1, X_2) = \frac{\sum_t [(X_1(t) - \overline{X}_1)(X_2(t-l) - \overline{X}_2)]}{\sqrt{\sum_t (X_1(t) - \overline{X}_1)^2 \sum_t (X_2(t-l) - \overline{X}_2)^2}}.$$

In the above summations, t is between $\max(1, l+1)$ and $\min(T, T-1)$. $\overline{X}_1$ and $\overline{X}_2$ are the average of $X_1(t)$ and $X_2(t)$ in this range for t respectively. For a set of curves that are tightly clustered and highly correlated, a small value of shift range s would be enough to capture the best pairwise shift correlation for all pairs. For some noisy curve sets, a large s is needed to achieve reasonable pairwise alignments. Thus, a different shift value s is used for different curve sets according to the degree of distribution in the peak of the curves. The value of s is automatically determined by the software in such a way that at least 90% of the curve peaks can be well aligned.

Mutation Detection:

The purpose of this study is to find rare mutations in exons. Theoretically, a DNA mutation would generate heteroduplex species and result in an addition band in the gel. However, the additional band may not add a new peak but only alter the shape of the band intensity curve. In order to detect this shape change, we adopt a k-nearest neighbor strategy. For all the curves corresponding to DNA homoduplexes, their shape should be similar to each other. Their shift correlation with each other, as defined above, should also be very high. Mutation curves, however, would have relatively lower shift correlations. The distance between two curves $X_1$ and $X_2$ is defined as $d(X_1, X_2) = 1 - c_x(X_1, X_2)$.

This distance would be 0 if the two curves were perfectly overlaid on each other and it gets larger as differences in the shape of the two curves increases. For a curve $X_i$, we define $d_i^{(k)}$ as the average distance of $x_i$ to its k nearest neighbors. For a single data set with several curves, the curve with the highest $d_i^{(k)}$ would have the highest probability of being associated with a mutation. Whereas, the value of $d_i^{(k)}$ strongly depends on how similar the curves are. In a data set where most curves are tightly clustered, one curve with a small shape difference may very possibly be an outlier that has a mutation in the DNA sequence. But its k-nearest neighbor distance may still be close to 0. In a data set where curves are widely distributed, many curves may have large k-nearest neighbor distances. Thus, the distance $d_i^{(k)}$ itself is not a good yardstick to determine whether a curve should be defined as an outlier with mutation. More specifically, the definition of an outlier should be related to the spread or diversity of the data set. Here we define a score based on the interquartile range (IQR) of $d^{(k)}=\{d_1^{(k)}, d_2^{(k)}, \ldots, d_m^{(k)}\}$ in each data set and use this score to sort the curves and define outliers. For a curve $X_i$, its similarity score $S_i^{(k)}$ is defined as $$S_i^{(k)}=[d_i^{(k)}-\text{Quantile}(d^{(k)},0.75)]/\text{IQR}(d^{(k)}),$$

$$\text{IQR}(d^{(k)})=\text{Quantile}(d^{(k)},0.75)-\text{Quantile}(d^{(k)},0.25),$$

where Quantile($d^{(k)}$,0.75) and Quantile($d^{(k)}$,0.25) are the 75% and 25% quantiles of $d^{(k)}$ respectively. It should be emphasized that the interquartile range is calculated for each data set separately. The similarity score $S_i^{(k)}$ is a monotone function of k-nearest neighbor distance $d_i^{(k)}$ and it reserves the order.

Another feature of curves with mutation is that the amplitude of the main peak is usually lower than that of normal curves. The reason for this is that, under the assumption of same sample amount, double-strand DNA with heterozygosity will have at least two forms after denaturation and renaturation. The different forms of double-strand DNA will run differently in a polyacrylamide gel. Thus the signal of the band on the gel will broaden and be less intense at the peak area compared with homozygous DNA. Thus, we can utilize this information in the mutation detection process by designing another similar score for curve peak intensity. For a curve $X_i$, denote its peak intensity as $h_i$ and denote $h=\{h_1, h_2, \ldots, h_m\}$. Intensity score $E_i$ is defined as $$E_i=[h_i-\text{Quantile}(h,0.75)]/\text{IQR}(h),$$

$$\text{IQR}(h)=\text{Quantile}(h,0.75)-\text{Quantile}(h,0.25).$$

So we define the final score $P_i$ as $$P_i=S_i^{(k)}+E_i.$$

This score combines the information of curve similarity and peak intensity. Since both scores use the interquartile range as a normalization constant, the final score is called the $P_i$ the IQR score. One advantage of IQR score is that it serves as a universal measure of how likely a curve is to be associated with DNA mutations. By incorporating the interquartile range of each data set, the IQR score automatically adjusts with data quality and variability. Curves from different data sets can be directly compared by their IQR scores and outliers with mutations reported by pooling all the IQR scores from all data sets together. Curves with higher IQR scores are more likely to be outliers, and thus the corresponding sequences are more likely to contain mutations.

The number of nearest neighbors k is determined by the frequency of mutation that we would like to detect. If no more than one mutation is expected in one data set, k should be set to 1. Although mutations are rare in a population level, the rate in the patient cohort samples may be higher. In this study, k=2.

Sequencing:

Fragments exhibiting an altered mobility pattern were re-amplified by cherry picking the appropriate DNA and primer combination using a Tecan Genesis robot. The primary reaction conditions were identical to the conditions used in the primary reactions used in the EGAN protocol. T7 pigtails (5'-GTAATACGACTCACTATAGGGGCGTAC-TAGCGTACCACGTGT-3') (SEQ ID NO:9) and T3 pigtails (5'-GATTAACCCTCACTAAAGGGAGAC-GATACGACGGGCGTACTA-3') (SEQ ID NO: 10) were incorporated in each fragment by a secondary amplification. A 10 μL reaction containing 1× HotstarTaq with 0.2 μM T7/T3 pigtail primers was set-up by tip-touching the primary reaction. Thermocycling conditions for the secondary amplification consisted of an initial denaturation step at 95° C. for 15 minutes followed by 25 cycles at 94° C. for 30 s, annealing at 60° C. for 45 s, and extension at 68.5° C. for 60 s and a final extension step at 72° C. for 10 minutes. PCR products were cleaned using the AMPure (Agencourt) protocol. The cleaned PCR products were eluted in 30 μL of 10 mM Tris pH 8.0.

The BigDye sequencing mixture consisted of a 1:5 solution of ABI BigDye and Better buffer (The Gel Company) with 1.6 μM T7 sequencing primer (5'-TAATACGACTCACTAT-AGGG-3') (SEQ ID NO:11) or 1.6 μM T3 sequencing primer (5'-ATTAACCCTCACTAAAGGGA-3') (SEQ ID NO:12). For each PCR fragment a 4 μL reaction (1:1 mixture of BigDye and PCR fragment) was prepared for the forward (T7) and reverse (T3) sequences. The ABI BigDye thermocycling conditions were used for the sequencing reaction. Sequencing reaction clean up was done according to the CleanSeq (Agencourt) protocol. Samples were eluted in water. Sequencing analysis was preformed using an ABI 3730xl DNA sequencer.

Results

Figure 4:
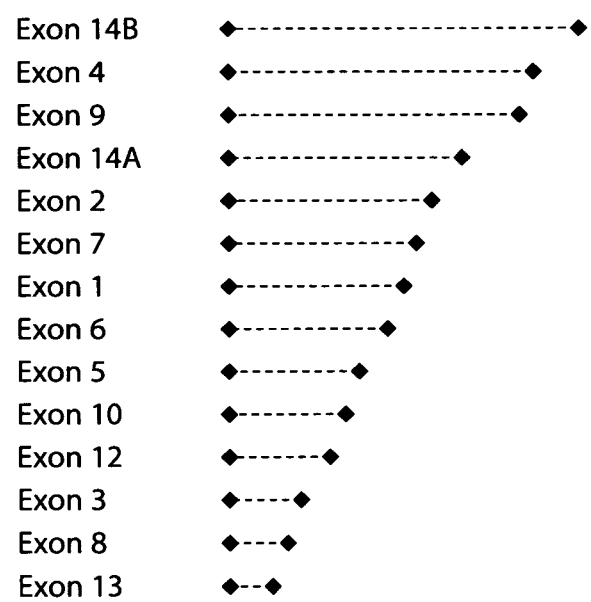
FIG. 4 is a schematic showing the mixture 14 example exons in one gel lane using different sized bands within each dye set as well as a mixture of the 3 dye sets.

Exon Grouping Analysis (EGAN) Process:

The procedure starts with the initial primer design. Primers are designed using variable amounts of intronic sequence to amplify exons with the highest possible PCR fragment size distribution. Post-PCR multiplexing of fluorescent labeled products results in efficient utilization each gel lane by analyzing as many exons as possible. FIG. 3 is a schematic of primer design leading to high throughput exon grouping of a 14 exon gene. An example is shown of primer pairs which are specific for exons in each dye set (Ned, 6-Fam and Vic). Each of the primer pairs is selected to amplify products of variable lengths to allow mixing and visualization in the same lane of an Exon Grouping Analysis (EGAN) gel. The first 13 exons are amplified using intronic primers while exon 14 is larger and split into 2 overlapping fragments. Since the three dye sets fluoresce at different wavelengths they can be mixed and visualized in that same lane of the gel. FIG. 4 demonstrates the fragment size and dye label distribution for analysis of this gene in one multiplexed lane.

BRCA1 and BRCA2 primers are picked using software designed in house based on iterative use of Primer3, a widely used program for designing PCR primers [2]. Specifically, exons larger than 450 base pairs are broken down into smaller fragments. All exons are then submitted to Primer3 in order to obtain products ranging in size from X to Y with an optimal spacing of 50 base pairs. Target regions that do not produce appropriately sized products are expanded or broken down further and resubmitted iteratively to Primer 3. The final output for BRCA1 and BRCA2 analysis includes primers that amplify large exons with multiple, overlapping PCR products and smaller exons by single PCR products.

Following primer selection specific tail sequences were added to forward and reverse primers during primer synthesis [1]. These tails were used to facilitate secondary amplification with the same set of fluorescent primers (FIG. 2) and avoid primer-dimer formation. Primers for 88 PCR fragments (34 BRCA1 and 54 BRCA2) were chosen to span the coding region of BRCA1 and BRCA2. The PCR fragments ranged from 232 to 558 base pairs in BRCA1 and 194 to 567 base pairs in BRCA2. Large exons, BRCA1 exon 11 and BRCA2 exons 10, 11, 14, 18 and 27, were amplified in several overlapping fragments. Each PCR fragment was labeled with a FAM, VIC, or NED fluorescent primer by a secondary PCR amplification and organized into 5 multiplexed PCR lanes, 2 lanes for BRCA1 (FIG. 5A) and 3 for BRCA2 (FIG. 5B). FIG. 5A and FIG. 5B show the actual EGAN pherogram of labeled PCR products mixed in each dye channel followed by the primer names and resulting product sizes for the BRCA1 and BRCA2 tests respectively. The multiplexed PCR groups were organized to maximize base pair separation between primers labeled in the same color. The complete set of primers used for BRCA1 and BRCA2 analysis with their respective dye labels are listed in Table 1. Final grouping of primers was dependent on measured EGAN gel mobility as there was variation from predicted size due to shape distortions in the EGAN gels.

Following primary, secondary amplification and post-PCR multiplexing fragments amplified from 95 patients are analyzed on five EGAN gels on ABI 377 sequencers (Applied Biosystems, Foster City, Calif.). FIG. 5 is a schematic depiction of Exon Grouping Analysis of amplified products. The EGAN gel composition is a variation of components described for Conformation Specific Gel Electrophoresis[3]. Homoduplexes and heteroduplexes generated from amplified products in 95 separate patients (S1-S95) are analyzed and compared to one another on a per exon basis. If no mutations are present, all the bands should contain the same homoduplexes and migrate at the same rate. Mutations present themselves as a mixture of homoduplexes and or heteroduplexes which have a different rate of migration due to alterations in DNA structure and which can be easily separated from the normal homoduplexes (see circled band corresponding to a mutation and its corresponding normal homoduplex in patient S10). Exons with aberrant mobility are then subjected to standard Sanger based DNA sequencing.

Exon Grouping Analysis (EGAN) Validation:

The gold standard for genetic analysis is Sanger based sequencing. In order to determine the sensitivity and specificity of EGAN a direct, blinded comparison was undertaken. Ninety-five DNA samples from a combination of breast cancer patients seen at the Dana Farber high risk clinic as well as controls were obtained at DFCI under IRB approved protocols (#93-085). Patient identifier information was coded and not made available to the laboratory. The blinded set of DNA samples were provided to the laboratory by Dr. Garber and clinical sequencing results as well as patient coding information were sent to Dr. Whittemore at Stanford. Full BRCA1 and BRCA2 EGAN tests were performed on all samples and coded laboratory results were submitted to Dr. Whittemore who decoded the results and determined sensitivity of the test. Results consisted of insertions, deletions, nonsense and missense mutations as well negative results.

Combined EGAN testing of BRCA1 and BRCA2 in 95 patients required 88 primary and 88 secondary amplifications for a total of 16,720 reactions. Fragments were multiplexed and electrophoresed and analyzed on ABI3730 XL sequencers using POP7 under denaturing conditions to quickly find insertions and deletions. The mixtures were also analyzed on five EGAN gels on ABI 377 sequencers. Sequencer files were the imported to the Data Acquisition and Data Analysis (DAx) software package (Van Mierlo Software Consultancy, Eindhoven, The Netherlands). DAx was used to construct and subtract baselines, convert the x-axis from migration time to base pair size, identify peaks, normalize and place peaks in individual bins. Bin sizes were designed to include a single PCR product as well as cover half the distance between the next smaller and the next larger product.

Figure 12A:
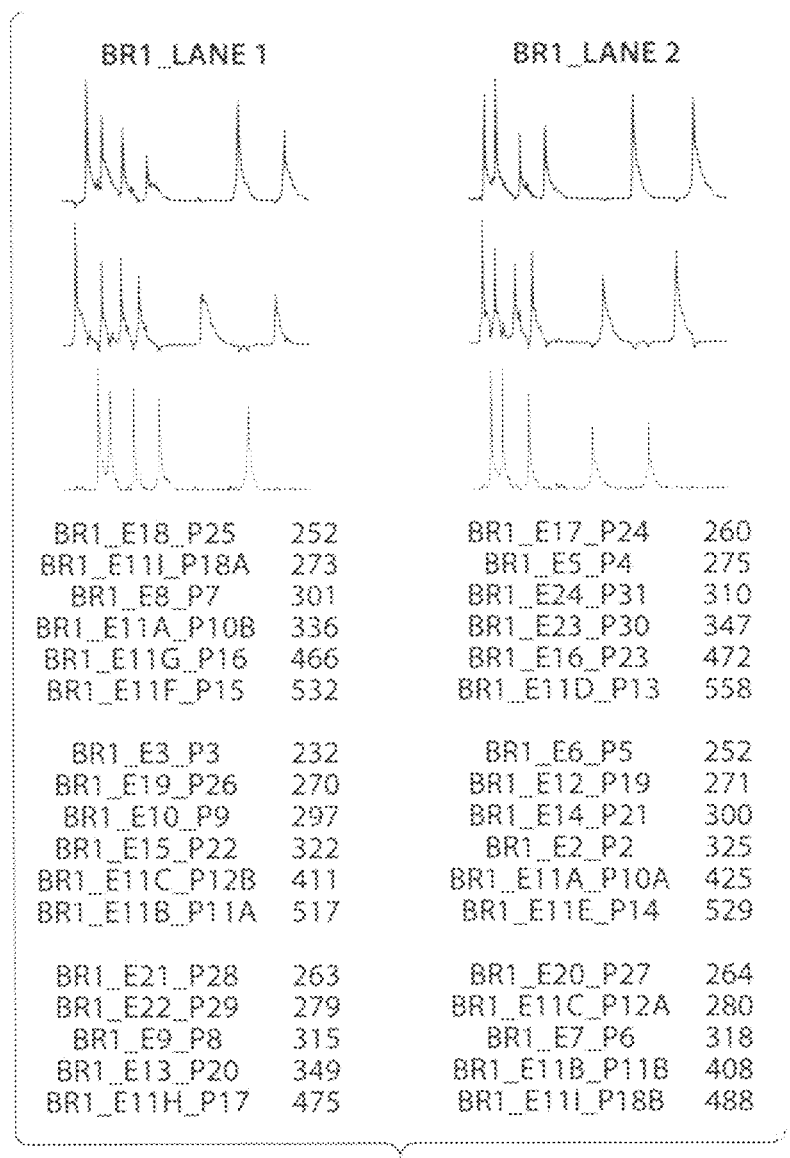
FIG. 12 depicts the results of organization of the BRCA1 and BRCA2 test. The PCR products are organized in five mixes which are analyzed in five gel lanes. A. The 2 multiplexed lanes for BRCA1. B. The 3 multiplexed lanes for BRCA2. The top of each panel shows the EGAN gel mobility of the combination of amplicons in each dye subset (Fam, Vic and Ned). The 3 sets of fluorescent amplicons in each lane are mixed together prior to EGAN gel loading. The amplicon names that are used make up each of the lanes and their fragment sizes on an EGAN gel are shown in each panel. Primer nomenclature is Gene Name (BR1=BRCA1, BR2=BRCA2)_Exon number_Primer # (labeled consecutively in gene).
Figure 12B:
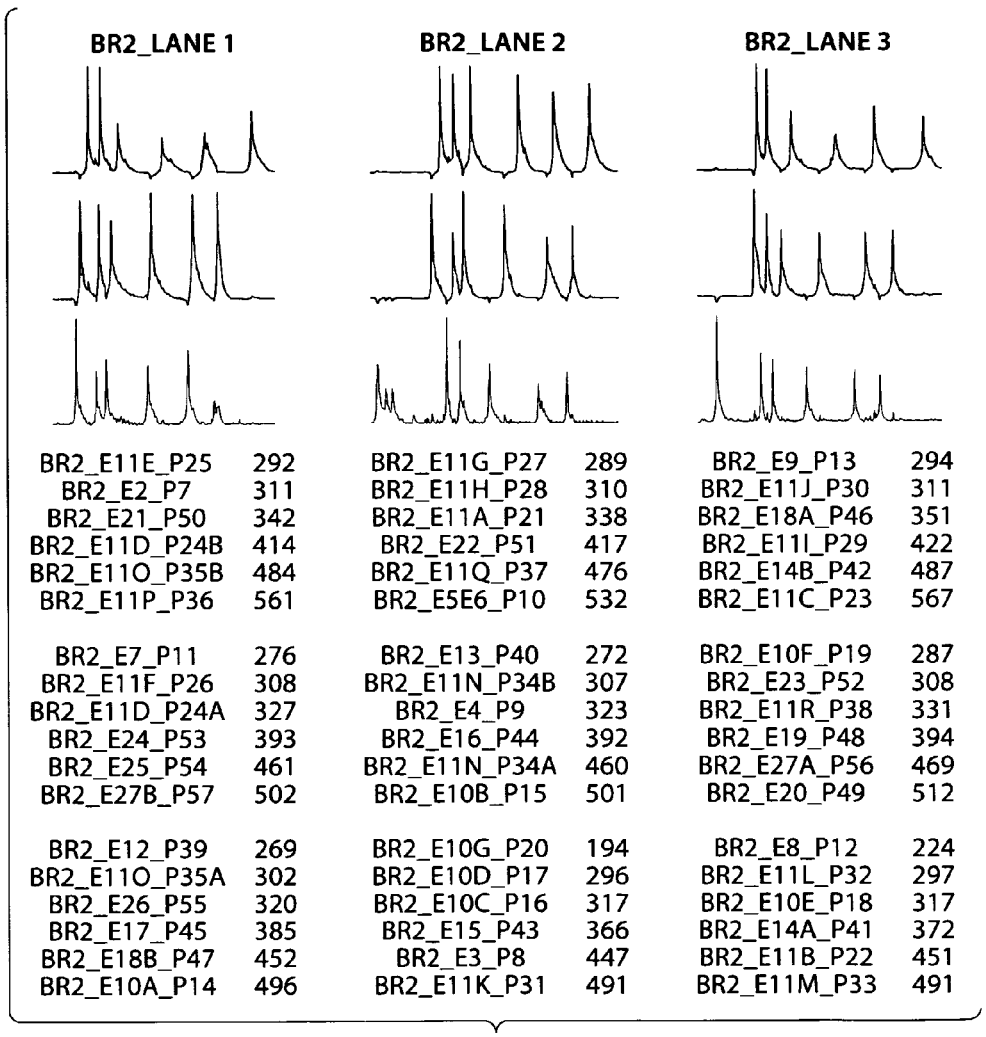
Figure 13A:
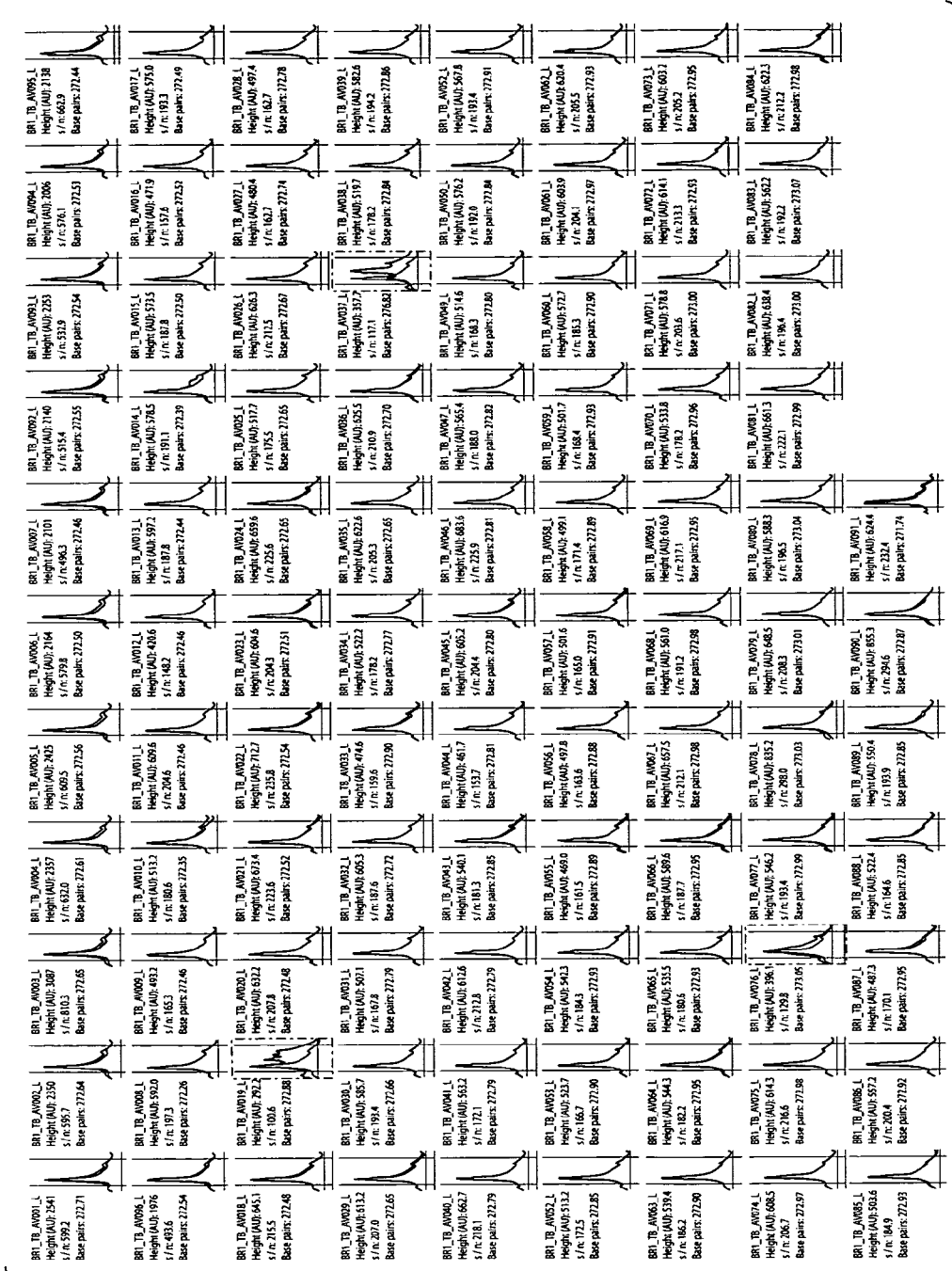
FIG. 13 depicts the visual output of EGAN analysis. A. Output from analysis of BRCA1 exon 5 compared in 95 patients using Dax software. 93 of 95 samples do not have alterations as can be seen from the lack of variation in the peak shapes. The presence of 3 mutations cause variation in the peak shapes and are highlighted in red. B. An example of the normal peak (labeled as "WT") as well as 3 single base changes are magnified. Note the aberrant shape varies by the nature of the mutation in each of the 3 cases.
Figure 13B:
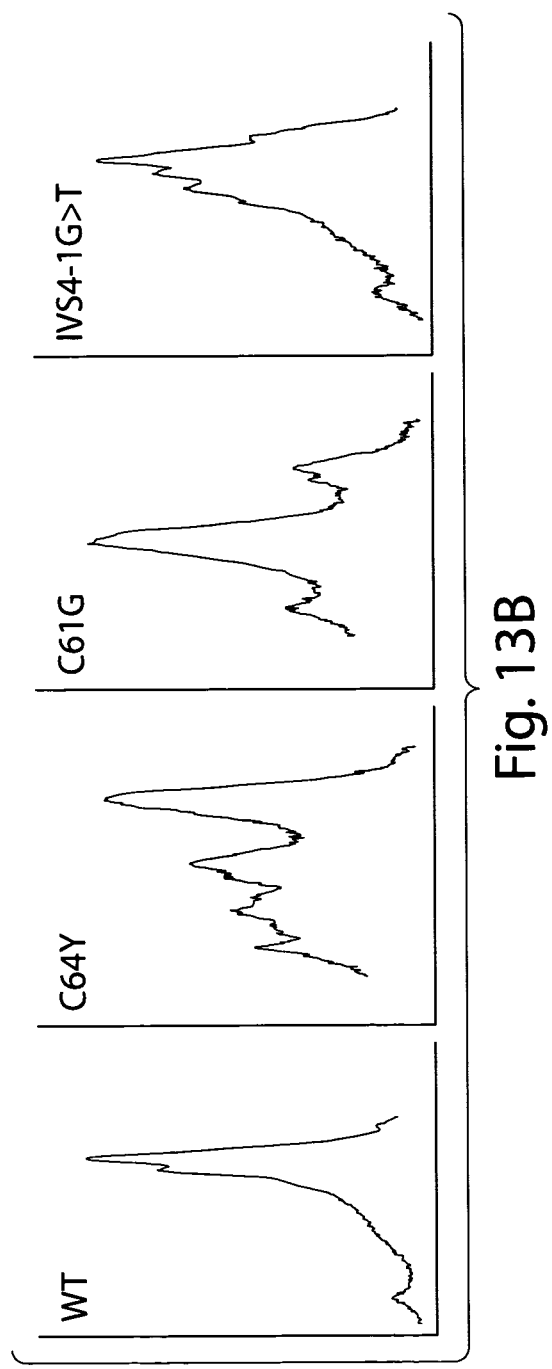

Once the peaks were organized into 88 bins which each contained 95 peaks representing data from each patient for that exon data was examined visually. FIG. 12 depicts sample EGAN output from analysis of BRCA1 exon 5 in 95 patients using Dax software. 92 of 95 samples do not have alterations as can be seen from the lack of variation in the peak shapes. The presence of 3 mutations causing variation in the peak shape and are highlighted in red in PANEL A. These aberrant peaks are magnified and highlighted in PANEL B. Note the aberrant shape varies by the nature of the mutation in each of the 3 cases, all of which represent clinically significant single base alterations. The IVS4-1 G>T splice site mutation as well as the C61Y and C64Y zinc finger domain missense mutations have a clearly aberrant shape when compared to a wild type band.

After visual analysis of all EGAN peaks a set of 150 out of the 8,360 were selected for sequencing resulting in a cost savings of 98.2% over direct sequencing alone. Comparison of the EGAN results to clinical sequencing results is shown in Table 1. There were a total of 64 clinically reportable alterations in BRCA1 and BRCA2 in this set of patients and both EGAN and clinical sequencing found 60 of those. Of the 4 remaining changes there was one large insertion (BRCA1 exon13 ins 6 kb) and one large deletion (BRCA1 exon 14-20 del 26 kb) that are not identifiable by either technique. Of the remaining 2 alterations visual EGAN analysis missed the S713X nonsense mutation while clinical sequencing analysis did not report the N55S uncharacterized variant. The sensitivities of both procedures are equivalent with 61 of 62 possible clinical alterations detected for an overall sensitivity of 98.4%.

Automated Peak Analysis:

Due to the difficult and time consuming visual analysis component of EGAN an automated peak analysis algorithm to assist with selection of products requiring downstream sequencing was developed. The EGAN output is represented by 88 curve sets (from 88 primers) containing 95 curves each (representing 95 patients) and only those fragments with mutations will exhibit a curve with distorted shape. Thus, an outlier detection method should be adequate to unveil the mutated fragments. Nevertheless, the nature of gel data makes the alignment and comparison of multiple curves uncontrollable by traditional methods. It is also difficult to compare the curves in different data sets. A method was developed that analyzes the curve data and systematically discovers outliers in each data set. Similarity between two curves is measured by maximum shift correlation. Curves in different data sets can be ranked together based on this correlation and interquartile range (IQR) in each set.

All 8360 exons have clinical sequencing results and 62 of them (0.74%) are confirmed to have clinically relevant alterations, including insertion, deletions, missense, nonsense and splicing changes. In the noise filtering step, 53 curves failed signal to noise ratio threshold analysis and were eliminated from further analysis. Since these sequences do not contain strong enough signals, they would be reanalyzed in EGAN gels or just directly sequenced. From 8307 remaining curves distributed in 88 data sets, our method can detect all of the 62 identifiable mutations. The bottom 3 IQR ranking mutations were BRCA1 4184del4, BRCA2 E1928X and BRCA1 S713X at 213, 225 and 512 respectively (Table 1). The BRCA1 S713X mutation in patient AV005 was identified using automated peak analysis in the top 6% of peaks as ranked by ROC scores even though it was missed by visual analysis.

Figure 14:
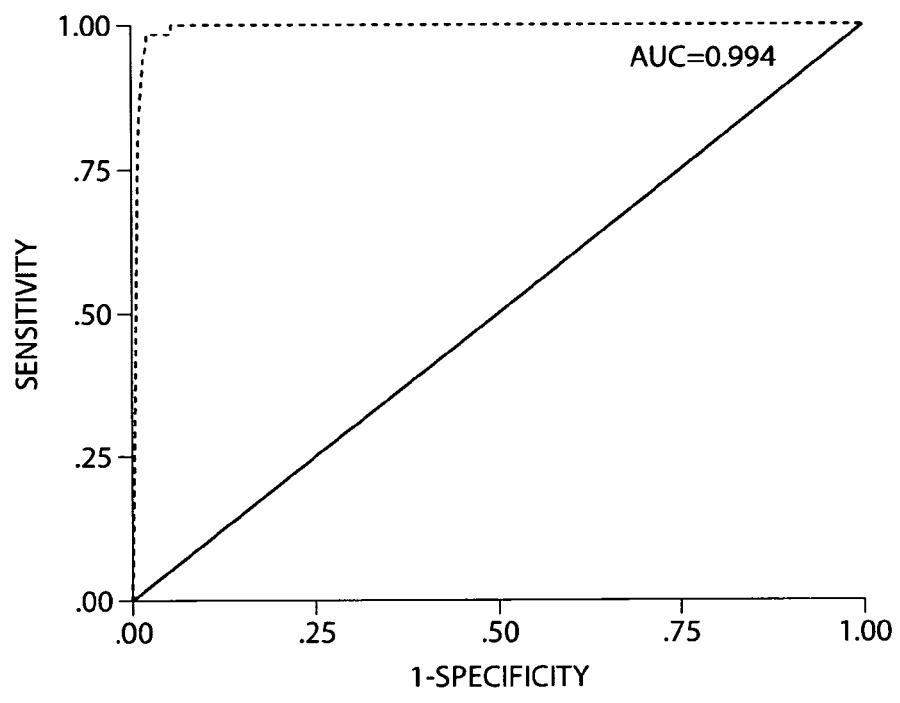
FIG. 14 is a ROC curve of the mutation prediction method of Exon Grouping Analysis (EGAN) for BRCA1 and BRCA2 mutation detection. Among 8307 samples, 62 contain clinically significant alterations. The 3 lowest ranking samples with alterations are 213, 225 and 512 (S713X missed by visual examination). The area under curve (AUC) is 0.994.
Figure 15:
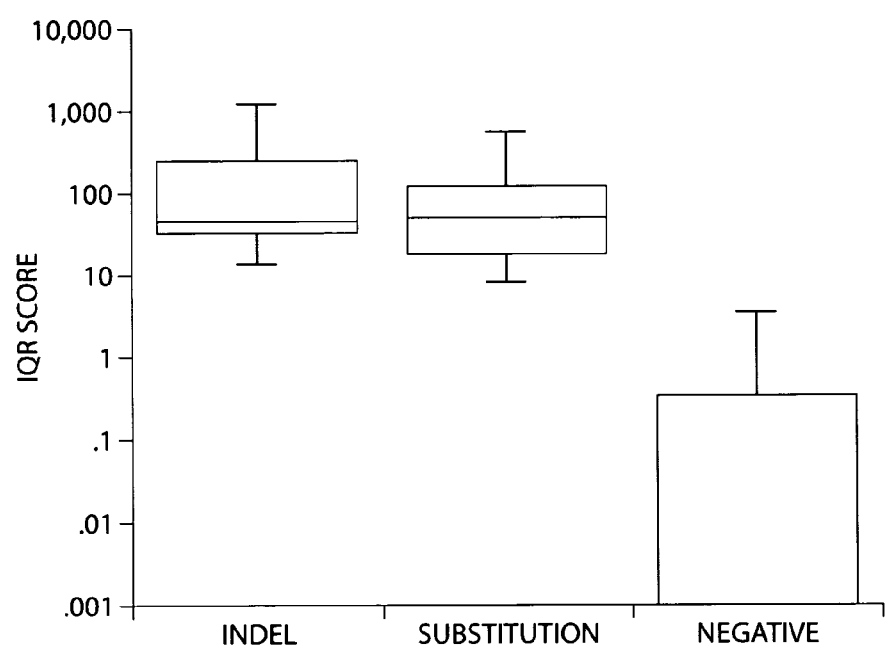
FIG. 15 is a bar chart showing the comparison of EGAN sensitivity for detection of insertions and deletion versus single base alterations. Boxplots of IQR scores for INDEL (insertions or deletions), SUBSTITUTION (Single base changes) and normal curves. The scores of the two groups are similar, and both are significantly different from the IQR scores of normal group.

Excellent performance characteristics of automated peak analysis are demonstrated using receiver operator curve analysis. FIG. 14 shows the Receiver-Operating Characteristic (ROC) curve of our method. ROC curve evaluates prediction performance, which in this study is the ability to discriminate curves corresponding to PCR fragments containing mutated DNA sequences from other wild type curves. Sensitivity against (1—specificity) is plotted at each level, and the area under the curve (AUC) is 0.994 (FIG. 14). This value means that, statistically, the band intensity curve of a randomly selected mutated sequence has lower score than the curve of a randomly selected non-mutated sequence 99.4% of the time, indicating very high sensitivity and specificity.

In order to evaluate how sensitive the EGAN method is to single base change, the IQR score for single base changes and insertion or deletions versus wild type fragments was compared. Among the 62 clinically reportable alterations, 25 of them are single base changes (substitutions) and the other 37 are insertions or deletions (INDEL). FIG. 14 shows the boxplots of IQR scores comparing indels with substitutions and negative results. The boxplots do not show a significant difference between the indel and substitution IQR scores. A Wilcoxon rank sum test gives a p-value of 0.249, suggesting that our method is sensitive not only to insertions or deletions, but also to single base changes. The scores of the two groups are similar, and both are significantly different from the IQR scores of normal group ($p<1\times10^{-6}$).

Ideally, an insertion or deletion would change the shape of a gel curve more dramatically than a single base change. This change should reflect in the IQR score we defined. The IQR score for INDELs and single base changes within each curve set was compared. For 26 pairs compared 16 times, INDELs have a higher IQR score than that of single base change (p=0.026). This comparison along with the above results implies that our method is working well. In the same curve set, if both some curves contain INDELs and some contain single base changes, the INDEL curves usually have higher IQR scores than single base change curves, and both of these two mutation types would be detected because their IQR scores are significantly higher than those of normal curves. When a curve set has only single base changes, even subtle changes would be enhanced such that curves with single base changes will have high IQR scores.

TABLE 1

| ID # | Primer | Gene | Designation | Result | Type | IQR Score | Rank |
|---|---|---|---|---|---|---|---|
| AV041 | BR2_E11Q_P37 | BRCA2 | 6674del5 | Positive | F | 1266.867024 | 3 |
| AV082 | BR2_E16_P44 | BRCA2 | 8019insA | Positive | F | 1219.935568 | 4 |
| AV034 | BR1_E18_P25 | BRCA1 | 5256delG | Positive | F | 1088.586276 | 5 |
| AV016 | BR1_E16_P23 | BRCA1 | 5083del19 | Positive | F | 1019.695819 | 6 |
| AV056 | BR2_E11H_P28 | BRCA2 | 3945delA | Positive | F | 746.257101 | 9 |
| AV037 | BR1_E5_P4 | BRCA1 | C61G | Positive | M | 733.862943 | 10 |
| AV067 | BR2_E11Q_P37 | BRCA2 | 6869insC | Positive | F | 699.931047 | 11 |
| AV033 | BR2_E9_P13 | BRCA2 | IVS9 + 1G > T | Positive | S | 554.348999 | 15 |
| AV050 | BR2_E20_P49 | BRCA2 | 8765delAG | Positive | F | 528.198803 | 17 |
| AV086 | BR2_E9_P13 | BRCA2 | IVS9 + 1G > A | Positive | S | 512.872386 | 20 |
| AV026 | BR2_E14A_P41 | BRCA2 | G2353R | Variant | M | 447.593395 | 22 |
| AV065 | BR2_E11C_P23 | BRCA2 | 2558insA | Positive | F | 346.586908 | 23 |
| AV025 | BR1_E7_P6 | BRCA1 | 448delAG | Positive | F | 312.682381 | 24 |
| AV019 | BR1_E5_P4 | BRCA1 | C64Y | Positive | M | 286.789083 | 28 |
| AV047 | BR2_E14A_P41 | BRCA2 | K2339N | Positive | M | 262.771074 | 29 |
| AV021 | BR2_E11A_P21 | BRCA2 | 2157delG | Positive | F | 247.754499 | 30 |
| AV071 | BR2_E11O_P35A | BRCA2 | 5823delAT | Positive | F | 233.93718 | 33 |
| AV084 | BR2_E10E_P18 | BRCA2 | T544I | Variant | M | 214.995484 | 34 |
| AV062 | BR2_E7_P11 | BRCA2 | W194X | Positive | N | 197.072036 | 36 |
| AV052 | BR2_E11K_P31 | BRCA2 | 4706del4 | Positive | F | 196.230118 | 37 |
| AV092 | BR1_E11B_P11A | BRCA1 | 1294del40 | Positive | F | 187.932791 | 39 |
| AV006 | BR2_E19_P48 | BRCA2 | IVS19 + 1G > A | Variant | S | 121.956253 | 50 |
| AV089 | BR1_E11R_P38 | BRCA2 | C2256X | Positive | N | 116.053559 | 52 |
| AV078 | BR2_E11D_P24A | BRCA2 | 3036del4 | Positive | F | 112.174205 | 53 |
| AV076 | BR1_E5_P4 | BRCA1 | IVS4 − 1G > T | Positive | S | 94.475792 | 56 |
| AV069 | BR2_E3_P8 | BRCA2 | N55S | Variant | M | 89.770593 | 57 |
| AV047 | BR2_E14B_P42 | BRCA2 | H2440R | Positive | M | 78.744639 | 61 |
| AV022 | BR1_E16_P23 | BRCA1 | Y1563X | Positive | N | 61.3563 | 65 |

TABLE 1-continued

| ID # | Primer | Gene | Designation | Result | Type | IQR Score | Rank |
|---|---|---|---|---|---|---|---|
| AV091 | BR1_E2_P2 | BRCA1 | 185delAG | Positive | F | 54.724071 | 69 |
| AV083 | BR2_E15_P43 | BRCA2 | R2520X | Positive | N | 50.381532 | 71 |
| AV090 | BR2_E15_P43 | BRCA2 | T2515I | Variant | M | 49.981312 | 72 |
| AV047 | BR2_E27A_P56 | BRCA2 | V3244I | Positive | M | 49.498819 | 73 |
| AV001 | BR2_E11O_P35B | BRCA2 | Y1894X | Positive | N | 47.715142 | 74 |
| AV058 | BR1_E20_P27 | BRCA1 | 5351del7ins12 | Positive | F | 46.944991 | 75 |
| AV075 | BR1_E16_P23 | BRCA1 | 5060delC | Positive | F | 44.57876 | 76 |
| AV003 | BR2_E11D_P24A | BRCA2 | D935H | Variant | M | 40.943863 | 81 |
| AV079 | BR1_E2_P2 | BRCA1 | 185delAG | Positive | F | 40.066396 | 82 |
| AV014 | BR1_E11H_P17 | BRCA1 | R1203X | Positive | N | 39.171774 | 83 |
| AV081 | BR2_E11_P_P36 | BRCA2 | 6174delT | Positive | F | 36.370808 | 88 |
| AV059 | BR2_E10B_P15 | BRCA2 | 1417ins4 | Positive | F | 35.94589 | 89 |
| AV093 | BR1_E15_P22 | BRCA1 | 4774del4 | Positive | F | 35.894308 | 90 |
| AV088 | BR1_E11H_P17 | BRCA1 | 3731delA | Positive | F | 35.834902 | 91 |
| AV008 | BR1_E11A_P10A | BRCA1 | 917delTT | Positive | F | 35.419611 | 92 |
| AV053 | BR1_E3_P3 | BRCA1 | 231delAA | Positive | F | 34.036844 | 96 |
| AV045 | BR1_E13_P20 | BRCA1 | R1443X | Positive | N | 32.907817 | 101 |
| AV004 | BR1_E2_P2 | BRCA1 | 185delAG | Positive | F | 32.500064 | 103 |
| AV072 | BR1_E2_P2 | BRCA1 | 185delAG | Positive | F | 32.438084 | 105 |
| AV028 | BR1_E11D_P13 | BRCA1 | 2295delC | Positive | F | 32.409101 | 106 |
| AV087 | BR1_E3_P8 | BRCA2 | A75P | Variant | M | 32.053396 | 107 |
| AV018 | BR2_E11_P_P36 | BRCA2 | 6174delT | Positive | F | 31.437608 | 108 |
| AV035 | BR2_E11_P_P36 | BRCA2 | 6174delT | Positive | F | 26.101803 | 119 |
| AV066 | BR1_E11I_P18B | BRCA1 | 4184del4 | Positive | F | 22.166775 | 128 |
| AV095 | BR2_E10F_P19 | BRCA2 | 2024del5 | Positive | F | 20.535422 | 132 |
| AV073 | BR1_E20_P27 | BRCA1 | 5382insC | Positive | F | 19.221793 | 138 |
| AV012 | BR2_E11O_P35B | BRCA2 | E1953X | Positive | N | 17.769521 | 146 |
| AV002 | BR1_E11C_P12B | BRCA1 | Q563X | Positive | N | 16.577765 | 156 |
| AV015 | BR1_E20_P27 | BRCA1 | 5382insC | Positive | F | 16.10759 | 157 |
| AV031 | BR1_E20_P27 | BRCA1 | 5382insC | Positive | F | 13.740944 | 173 |
| AV068 | BR1_E14_P21 | BRCA1 | R1495M | Positive | M | 10.305057 | 207 |
| AV064 | BR1_E11I_P18B | BRCA1 | 4184del4 | Positive | F | 9.627008 | 213 |
| AV024 | BR2_E11O_P35B | BRCA2 | E1928X | Positive | N | 8.643731 | 225 |
| AV005 | BR1_E11D_P13 | BRCA1 | S713X | Positive | N | 3.321473 | 512 |
| AV070 | NA | BRCA1 | exon 14-20 del 26 kb | Positive | LG DEL | NA | NA |
| AV077 | NA | BRCA1 | exon 13 ins 6 kb | Positive | LG INS | NA | NA |

The columns the table are as follows: ID# represents the lab identifier for each of the 95 patients tested. Primer represents the primer name with the designation of Gene_Exon#_Primer#. Designation is the mutation name. Result decits either Positive or Uncharacterized Variant clinical results. Type describes the kind of alteration. Either Missense, Nonsense, Splice, Frameshift, Large insertion or Large deletion. IQR Score is the interquartile score where larger numbers indicate greater divergence in the peak shape as compared to other analyses of that same PCR amplicon. Code is a confidence ranking from 1 (lowest) to 5 (highest) that indicates the presence of a mutation. The Rank reflects the order of the IQR score among the 8800 PCR products tested. Large insertions and deletions that are not identifiable by either clinical sequencing or EGAN are highlighted in bold. Italic font indicates the 2 patients with discrepancies in EGAN and sequencing analysis. S713X in AV005 was missed by EGAN using visual inspection of the peaks. N55S was a variant which was not reported in the patient AV069 clinical report based on standard sequencing.

REFERENCES

1. Brownie, J., et al., *The elimination of primer-dimer accumulation in PCR*. Nucleic Acids Res, 1997.25(16): p. 3235-41.
2. Rozen, S. and H. Skaletsky, *Primer3 on the WWW for general users and for biologist programmers*. Methods Mol Biol, 2000. 132: p. 365-86.
3. Korkko, J., et al., *Conformation sensitive gel electrophoresis for simple and accurate detection of mutations: comparison with denaturing gradient gel electrophoresis and nucleotide sequencing*. Proc Natl Acad Sci USA, 1998. 95(4): p. 1681-5.

All patent applications, patents, and literature references cited in this specification are hereby incorporated by reference in their entirety.

The invention claimed is:

1. A method for detecting one or more sequence changes in a plurality of target nucleic acid sequences in a nucleic acid sample comprising the steps of:
   a) performing a multiplexed PCR reaction on the nucleic acid sample in the presence of a plurality of target specific PCR primer pairs, wherein each said target specific PCR primer pair comprises a first and a second target specific primer and is specific for one of said plurality of target nucleic acid sequences to generate a plurality of amplified products; wherein said first target specific primer comprises a first 5' region which contains the same sequence for all first target specific primers of said plurality of target specific PCR primer pairs and a first 3' region specific for said one of the plurality of target nucleic acid sequences; said second target specific primer comprises a second 5' region which contains the same sequence for all second target specific primers of said plurality of target specific PCR primer pairs and a second 3' region specific for said one of the plurality of target nucleic acid sequences, and wherein said first 5' region of said first target specific primer and said second 5' region of said second target specific primer are different from each other;
   b) performing a PCR reaction on said plurality of amplified products with a first and a second amplified product specific primer which are specific for said plurality of amplified products; wherein the first amplified product specific primer comprises a 3' region identical to the first 5' region of the first target specific primer, the second amplified product specific primer comprises a 3' region identical to the second 5' region of the second target specific primer;
   c) generating homoduplexes and heteroduplexes from the amplified products; and
   d) detecting the presence of the heteroduplexes as an indicator of the one or more sequence changes.

2. The method of claim 1 wherein steps a and b are performed simultaneously in the same reaction.

3. The method of claim 1 wherein steps a and b are performed in different reactions.

4. The method of claim 1 where each target specific PCR primer pair produces an amplified product in a PCR reaction of a different length than each other target specific PCR primer pair.

5. The method of claim 1 wherein step a is performed with at least 5 target specific primer pairs.

6. The method of claim 1 wherein step a is performed with at least 10 target specific primer pairs, at least 20 target specific primer pairs, at least 30 target specific primer pairs, at least 40 target specific primer pairs, at least 60 target specific primer pairs, at least 80 target specific primer pairs, or at least 100 target specific primer pairs.

7. The method of claim 1 wherein the plurality of amplified products are between 200 to 800 by in length.

8. The method of claim 1 wherein first amplified product specific primer or the second amplified product specific primer comprises a detectable label.

9. The method of claim 8 wherein the detectable label is selected from the group consisting a fluorophore, an enzyme, a quencher, an enzyme inhibitor, a radioactive label, a member of a binding pair, and a combination thereof.

10. The method of claim 1 wherein said generating step comprises
   c1) denaturing the plurality of amplified products to form single stranded amplified products; and
   c2) annealing said single stranded amplified products to each other to form homoduplexes and heteroduplexes.

11. The method of claim 10 wherein denaturing is perform by heating the amplified products.

12. The method of claim 10 wherein annealing is performed by incubating the amplified products at 68° C for 30 minutes.

13. The method of claim 1 wherein detecting the presence of heteroduplexes in step d comprises detecting a difference in migration speed between the homoduplexes and the heteroduplexes under conformation sensitive gel electrophoresis.

14. The method of claim 13 wherein the conformation sensitive gel electrophoresis is performed in a capillary containing a flowable polymer.

15. The method of claim 13 wherein the conformation sensitive gel electrophoresis is performed in a gel comprising polyacrylamide with a 99 to 1 ratio of acrylamide to BAP, 15% formamide, and 1×TBE.

16. The method of claim 15 wherein the polyacrylamide is at a concentration of between 6% to 15%.

17. The method of claim 1 wherein the one or more sequence changes is selected from the group consisting of an alteration of one or more bases, an insertion of one or more bases, a deletion of one or more bases, and combinations thereof.

18. The method of claim 1 further comprising the step of determining the nucleic acid sequence of said heteroduplexes to determine the one or more sequence changes.

19. The method of claim 18 wherein determining the nucleic acid sequence comprises the step of sequencing said amplified product or said target nucleic acid using an amplified product specific primer.

20. The method of claim 1 wherein said nucleic acid sample is isolated from a patient suspected of a genetic disease.

21. The method of claim 20 wherein the genetic disease is selected from the group consisting of cancer, cystic fibrosis, sickle-cell anemia, 13-thalassemia, and Gaucher's disease.

22. The method of claim 1 wherein at least one target nucleic acid sequence of the plurality of target nucleic acid sequences is a part of a gene selected from the group consisting of an oncogene, beta-globin, cystic fibrosis transmembrane conductance regulator receptor, glucocerebrosidase and a combination thereof.

23. The method of claim 1 wherein the method detects one or more sequence changes in at least one oncogene.

24. The method in claim 23 wherein the oncogene is selected from the group consisting of BRCA1, BRCA2, RAS, and a combination thereof.

25. The method of claim 1 wherein the plurality of target nucleic acid sequences are RNA.

26. The method of claim 25 wherein the RNA is a mRNA.

27. A method for detecting one or more sequence changes in a diseased tissue comprising the steps of:
   a) performing the method of claim 1 on a nucleic acid sample isolated from the diseased tissue to detect the presences of diseased tissue heteroduplexes and homoduplexes;
   b) performing the method of claim 1 on a nucleic acid sample isolated from a normal tissue to detect the presence of normal tissue heteroduplexes and homoduplexes;
   c) comparing the heteroduplexes and homoduplexes of step a with the heteroduplexes and homoduplexes of step b to determine a difference which is indicative of one or more sequence changes;
   wherein steps (a) and (b) are performed in any order.

28. The method of claim 27 wherein the diseased tissue and the normal tissue are from the same subject.

29. The method of claim 27 wherein the diseased tissue and the normal tissue are from different subjects.

30. The method of claim 27 wherein the diseased tissue and the normal tissue are of the same tissue type.

* * * * *